(12) United States Patent
Ma et al.

(10) Patent No.: US 11,040,019 B2
(45) Date of Patent: Jun. 22, 2021

(54) SELECTIVE ESTROGEN-RECEPTOR MODULATORS (SERMS) CONFER PROTECTION AGAINST PHOTORECEPTOR DEGENERATION

(71) Applicant: THE UNITED STATES OF AMERICA, as represented by the Secretary, Department of Health and Human Services, Bethesda, MD (US)

(72) Inventors: Wenxin Ma, Potomac, MD (US); Lian Zhao, Kensington, MD (US); Xu Wang, Falls Church, VA (US); Wai T. Wong, Philadelphia, PA (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 149 days.

(21) Appl. No.: 16/325,678

(22) PCT Filed: Aug. 10, 2017

(86) PCT No.: PCT/US2017/046359
§ 371 (c)(1),
(2) Date: Feb. 14, 2019

(87) PCT Pub. No.: WO2018/034945
PCT Pub. Date: Feb. 22, 2018

(65) Prior Publication Data
US 2019/0209497 A1    Jul. 11, 2019

Related U.S. Application Data

(60) Provisional application No. 62/377,439, filed on Aug. 19, 2016.

(51) Int. Cl.
*A61K 31/138* (2006.01)
*A61K 31/4535* (2006.01)
(Continued)

(52) U.S. Cl.
CPC ............ *A61K 31/138* (2013.01); *A61B 5/398* (2021.01); *A61B 5/4848* (2013.01);
(Continued)

(58) Field of Classification Search
CPC .. A61K 31/138; A61K 31/55; A61K 31/4535; A61P 27/02; A61B 5/0496; A61B 5/4848
(Continued)

(56) References Cited

U.S. PATENT DOCUMENTS

| 4,852,579 A | 8/1989 | Gilstad et al. |
| 2003/0032676 A1 | 2/2003 | Kimelberg et al. |

(Continued)

FOREIGN PATENT DOCUMENTS

| CA | 2288631 | 11/1999 |
| CN | 103211803 A | 7/2013 |

(Continued)

OTHER PUBLICATIONS

Broughton, "Watch for ocular effects of breast cancer drugs," *Eyenet* 27-29 (Mar. 2013).
(Continued)

*Primary Examiner* — Taylor V Oh
(74) *Attorney, Agent, or Firm* — Klarquist Sparkman, LLP

(57) ABSTRACT

Methods are disclosed for treating and/or preventing retinal degeneration is a subject. In some embodiments, the method includes administering to the subject a therapeutically effective amount of a selective estrogen receptor modulator (SERM) to treat the retinal degeneration in the subject. In other embodiments, the SERM is administered orally. In
(Continued)

some examples, the SERM is tamoxifen, afimoxifene, raloxifene, bazedoxifene, arzoxifene, desmethylarzoxifene, or a salt or derivative thereof, or combinations thereof.

18 Claims, 18 Drawing Sheets

(51) Int. Cl.
    *A61K 31/55*     (2006.01)
    *A61B 5/398*     (2021.01)
    *A61P 27/02*     (2006.01)
    *A61B 5/00*     (2006.01)

(52) U.S. Cl.
    CPC .......... *A61K 31/4535* (2013.01); *A61K 31/55* (2013.01); *A61P 27/02* (2018.01)

(58) Field of Classification Search
    USPC .......................................................... 514/324
    See application file for complete search history.

(56) References Cited

U.S. PATENT DOCUMENTS

| | | |
|---|---|---|
| 2005/0244461 A1 | 11/2005 | Nivaggioli et al. |
| 2006/0002963 A1 | 1/2006 | Rabinovich-Guilatt et al. |
| 2010/0267767 A1 | 10/2010 | Narayanan et al. |
| 2013/0338145 A1 | 12/2013 | Mitchell et al. |
| 2014/0199277 A1* | 7/2014 | Cosma .................... A61P 27/06 424/93.7 |

FOREIGN PATENT DOCUMENTS

| | | | | |
|---|---|---|---|---|
| WO | WO 1998/50065 | | 12/1998 | |
| WO | WO 2002/34266 A1 | | 5/2002 | |
| WO | WO 2007/062230 A2 | | 5/2007 | |
| WO | WO-2011113904 A1 * | | 9/2011 | .............. A61P 27/02 |
| WO | WO 2016/064959 A1 | | 4/2016 | |

OTHER PUBLICATIONS

Giddabasappa et al., "Receptor modulator (SERM) inhibits retinal neovascularization in the mouse model of oxygen induced retinopathy," *ARVO Annual Meeting Abstract*, 2 pages (Apr. 2010).
International Search Report from parent PCT Application No. PCT/US2017/046359, 4 pages (dated Nov. 7, 2017).
Jin et al., "Friend or foe? Resident microglia vs bone marrow-derived microglia and their roles in the retinal degeneration," *Mol Neurobiol* 54:4094-4112 (e-PUB Jun. 18, 2016).
Kim et al., "Tamoxifen toxicity in cultured retinal pigment epithelial cells is mediated by concurrent regulated cell death mechanisms," *IVOS* 55(8): 4747-4758 (Aug. 2014).
Koch et al., "Halting progressive neurodegeneration in advanced retinitis pigmentosa," Journal of Clinical Investigation 125(9): 3704-3713 (Sep. 2015).
Longbottom et al., "Genetic ablation of retinal pigment epithelial cells reveals the adaptive response of the epithelium and impact on photoreceptors," *PNAS* 106(44): 18728-18733 (Nov. 3, 2009).
Omoti and Omoti, "Ocular toxicity of systemic anticancer chemotherapy," *Pharmacy Practice* 4(2): 55-59 (2006).
Salgado et al., "Tamoxifen and Src kinase inhibitors as neuroprotective/neuroregenerative drugs after spinal cord injury," *Neural Regeneration Research* 10(3): 385-390 (Mar. 2015).
Wang et al., "Requirement for microglia for the maintenance of synaptic function and integrity in the mature retina," *Journal of Neuroscience* 36(9):2827-2842 (Mar. 2, 2016).
Wang et al., "Tamoxifen provides structural and functional rescue in murine models of photoreceptor degeneration," *Journal of Neuroscience* 37(12) :3294-3310 (Mar. 22, 2017).
Written Opinion from parent PCT Application No. PCT/US2017/046359, 6 pages (dated Nov. 7, 2017).

* cited by examiner

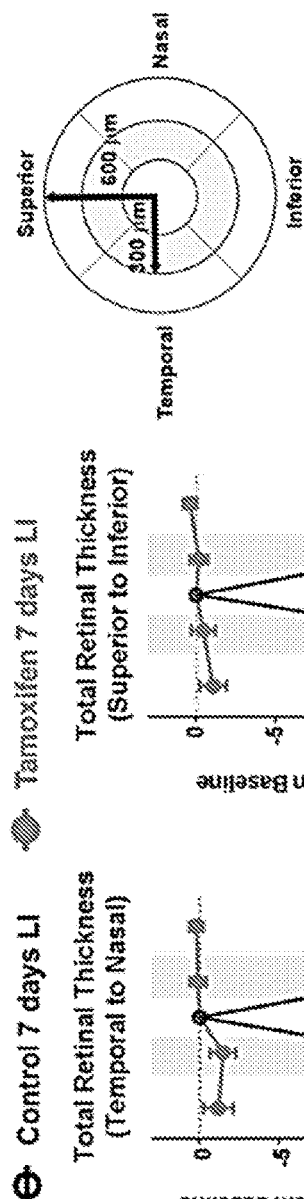
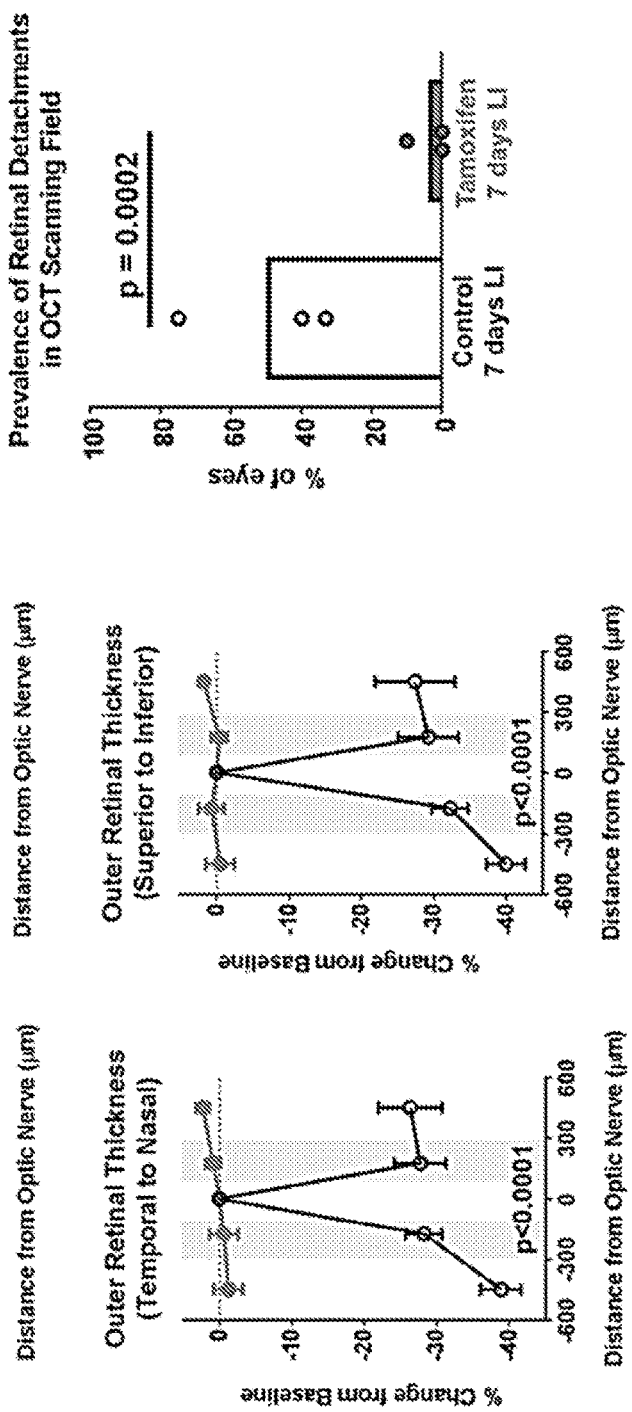
FIG. 1C
FIG. 1D

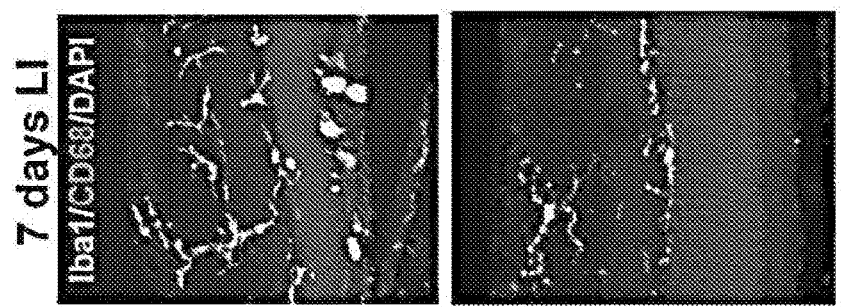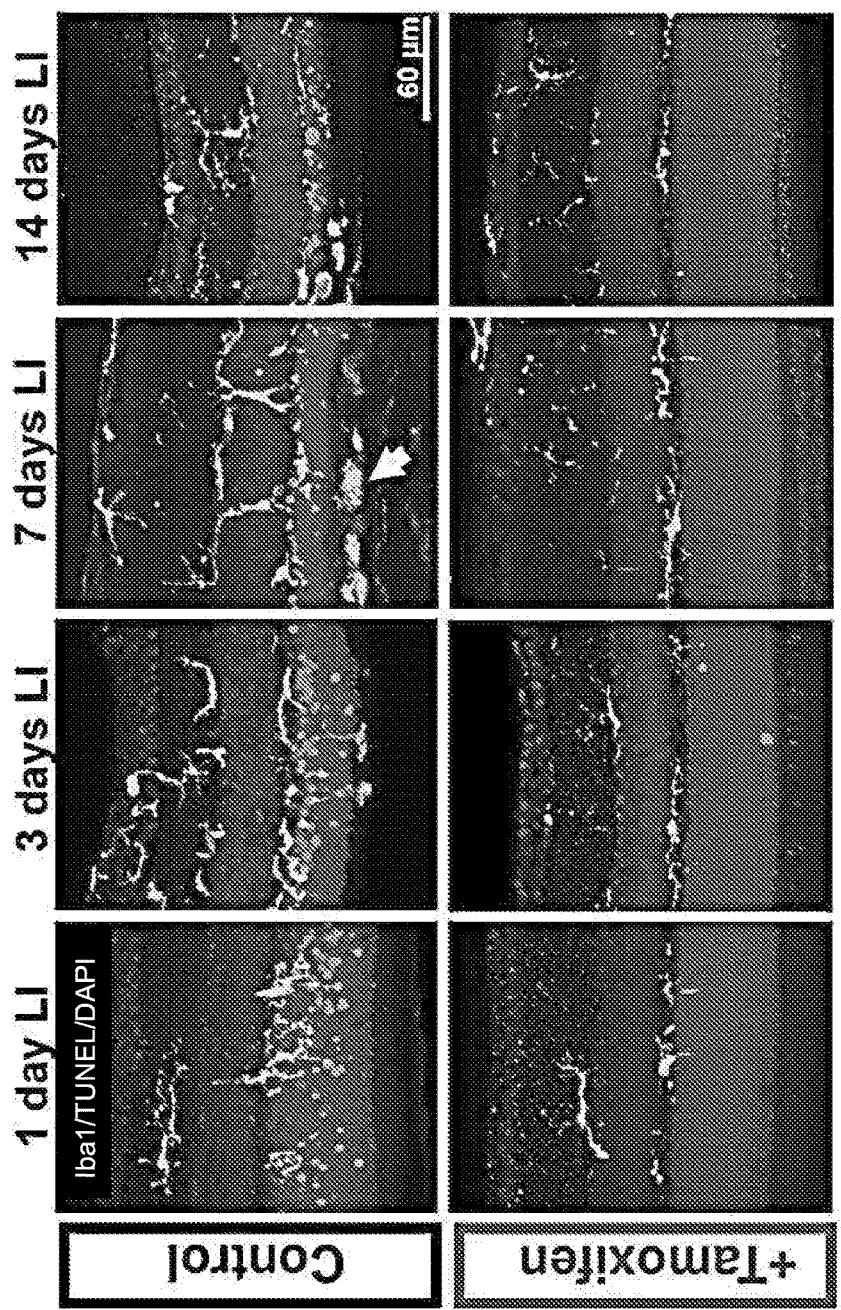

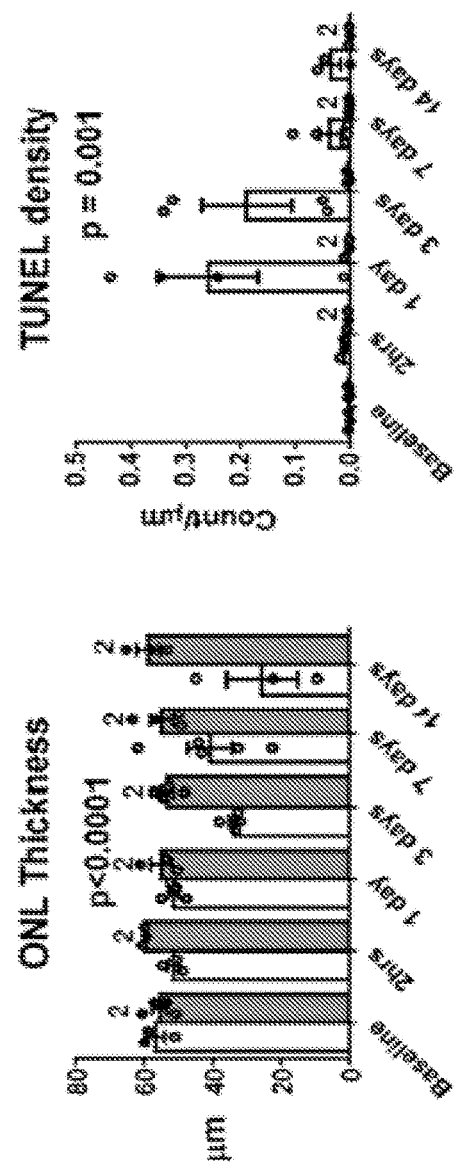
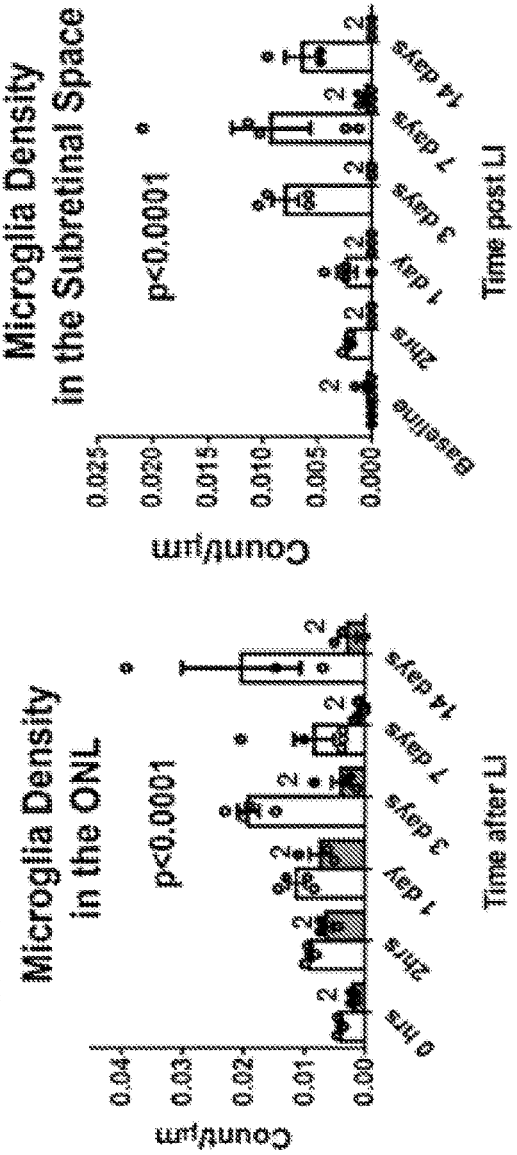
FIG. 2E FIG. 2F FIG. 2G FIG. 2H FIG. 2I

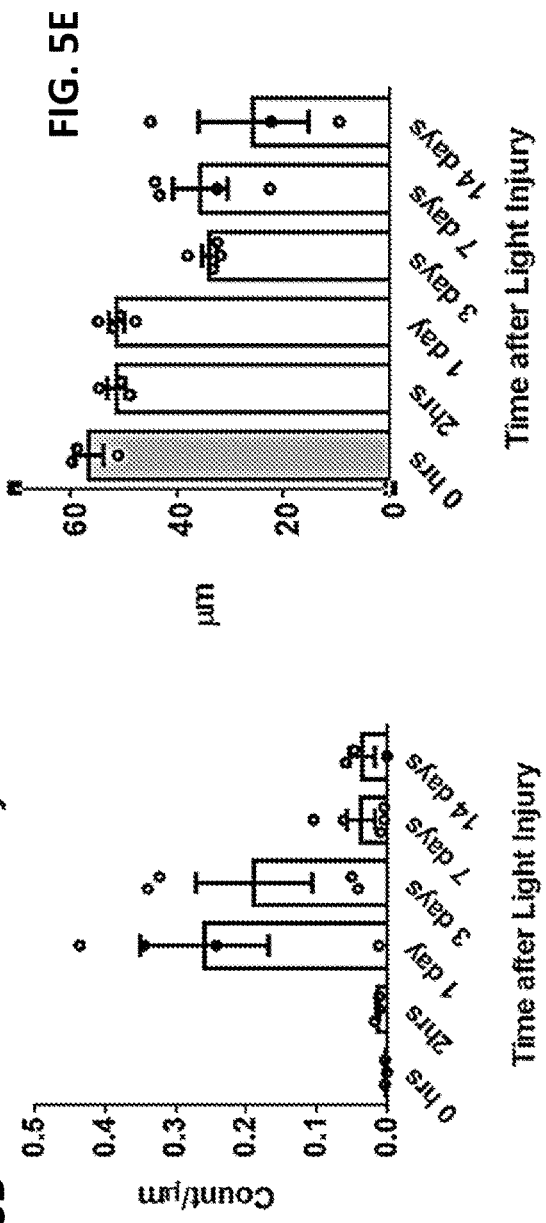
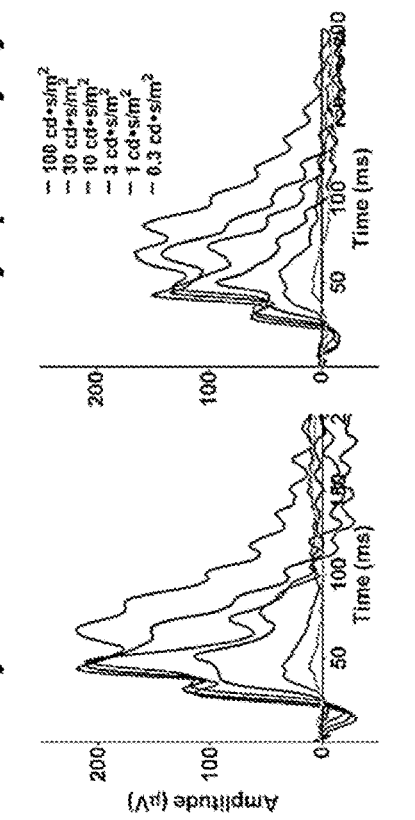
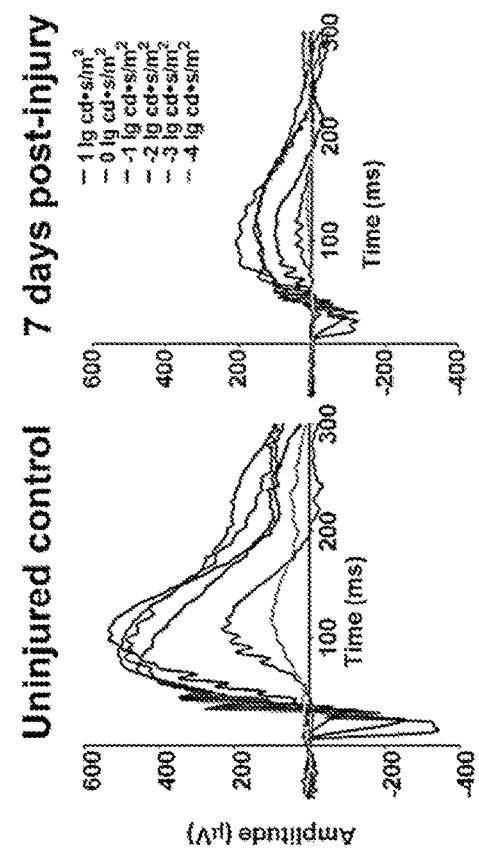
FIG. 5D  FIG. 5E  FIG. 5F  FIG. 5G

Change in Total Retinal Thickness following LI

SELECTIVE ESTROGEN-RECEPTOR MODULATORS (SERMS) CONFER PROTECTION AGAINST PHOTORECEPTOR DEGENERATION

CROSS REFERENCE TO RELATED APPLICATION

This is a § 371 U.S. national stage of International Application No. PCT/US2017/046359, filed Aug. 10, 2017, which was published in English under PCT Article 21(2), and which application claims the benefit of U.S. Provisional Application No. 62/377,439, filed Aug. 19, 2016, which is incorporated by reference herein in its entirety.

FIELD OF THE DISCLOSURE

This relates to the field of treatment and/or prevention of retinal degeneration using SERMS, such as tamoxifen or a salt or derivative thereof, or raloxifene or a salt or derivative thereof.

BACKGROUND

Degeneration of photoreceptors, the light-sensitive neurons in the retina, is a prominent feature in diseases of the retina contributing significantly to irreversible blindness worldwide (Congdon et al., Archives of Ophthalmology 122:477-48, 2004; Jonas et al., American Journal of Ophthalmology 158:808-815, 2014). Photoreceptor degeneration occurs in a variety of retinal conditions ranging from atrophic age-related macular degeneration (AMD) and diabetic maculopathy, where death of macular photoreceptors results in central vision loss, to retinitis pigmentosa (RP), in which widespread photoreceptor degeneration across the entire retina leads to total blindness. The cellular mechanisms underlying photoreceptor degeneration in these diseases are incompletely understood and comprehensive treatments that slow down or arrest the progression of degeneration are still unavailable (Holz et al., Ophthalmology 121:1079-1091, 2014; Wert et al., Developments in Ophthalmology 53:33-43, 2014). Currently, affected patients such as those with atrophic AMD and RP typically receive no treatment and progress with time to visual deficits ranging from severe vision loss to total blindness.

Studies of human disease and animal models of photoreceptor degeneration (Roque et al., 1996) have discovered that photoreceptor loss is often accompanied by chronic neuroinflammatory changes, including increases in levels of proinflammatory cytokines (Yoshida et al., Ophthalmology 120:100-105, 2013; Yoshida et al., Ophthalmology 120:e5-12, 2013 and the infiltration of retinal microglia into the photoreceptor layer where they interact closely with degenerating photoreceptors (Roque et al., Invest Ophthalmol Vis Sci 37:196-203, 1996; Gupta et al., Exp Eye Res 76:463-47, 2003). We have found previously that these infiltrating retinal microglia become activated and contribute actively to photoreceptor demise via the phagocytosis and clearance of viable photoreceptors and the secretion of pro-inflammatory cytokines that potentiate photoreceptor apoptosis (Zhao et al., EMBO Molecular Medicine, 7:1179-97. 2015; Zabel et al., Glia, 64:1479-91 2016). In rodent models of disease, measures that modulate their phagocytic activity (Zabel et al., supra, 2016), or reduce their activation status (Peng et al., The Journal of Neuroscience: The Official Journal of the Society for Neuroscience 34:8139-8150, 2014; Scholz et al., Journal of Neuroinflammation 12:209, 2015) have been demonstrated to ameliorate the rate of photoreceptor loss. However, a need remains for additional agents that can be used to treat diseases that include photoreceptor loss.

SUMMARY OF THE DISCLOSURE

It is disclosed herein that tamoxifen, a drug previously associated with retina toxicity, confers significant structural and functional protection to photoreceptors in both acute and genetic models of photoreceptor degeneration. Thus, tamoxifen, and other SERMs with the same activities, can be used therapeutically, such as for the neuroprotection of endangered photoreceptors. In addition, methods are disclosed for treating or preventing retinal degeneration in a subject. The subject can have retinitis pigmentosa, atrophic macular degeneration, or any other retinal disease in which neuroinflammation drives neuronal loss.

In one embodiment, a method is disclosed for treating and/or preventing retinal degeneration is a subject. The method includes administering to the subject a therapeutically effective amount of a selective estrogen receptor modulator (SERM) to treat the retinal degeneration in the subject. In specific examples, the SERM is one or more of tamoxifen, afimoxifene, raloxifene, bazedoxifene, arzoxifene, desmethylarzoxifene, or a salt or derivative thereof. In specific non-limiting examples, the subject does not have cancer, such as breast cancer. In additional non-limiting examples, the subject is human.

In some embodiments SERM is administered orally. In some embodiments, the SERM is tamoxifen or a salt or derivate thereof. In specific non-limiting examples, tamoxifen, salt or derivative thereof is administered orally, such as at a dose of 40 mg/kg to 80 mg per kg daily.

The foregoing and other features of the disclosure will become more apparent from the following detailed description of several embodiments which proceeds with reference to the accompanying figures.

BRIEF DESCRIPTION OF THE FIGURES

FIGS. 1A-1E. Tamoxifen administration prior to acute light injury results in near complete rescue of structural and functional retinal damage. Adult mice were administered daily oral tamoxifen (added to standard animal chow, 500 mg per kg of chow, estimated intake of 80 mg/kg body weight/day) 1 week prior to light injury and thereafter; control animals were fed standard chow without tamoxifen at all time points. (A) Total retinal thickness in the central retina (radius 600 μm around optic nerve) as measured by OCT are depicted in heat maps; control animals demonstrate extensive retinal thinning at 7 days post-LI that was absent in tamoxifen-treated animals. (B) Individual OCT B-scans in the superior retina demonstrated: (1) loss of outer segments, (2) thinning of the ONL layer (white box), and (3) emergence of areas of retinal detachment (white arrow); these features were absent in tamoxifen-treated animals (grey box). (C) Quantification of mean OCT-derived total (top row) and outer retina thickness (bottom row) in inner and outer quadrants in the horizontal (left panels) and vertical (right panels) axes demonstrate marked thinning 7 days post-LI in control animals (black lines) but no significant changes from baseline in tamoxifen-treated animals (grey lines) (n=27 eyes from 14 animals of mixed gender for each group, 2-way ANOVA). (D) The prevalence of localized retinal detachments, scored at 7 days post-LI, was significantly lower in tamoxifen-treated vs. control groups (n=27 eyes in each group in 3 independent experiments, Chi-square statistic). (E) ERG demonstrates that a- and b-wave amplitudes for dark- and light-adapted functional responses obtained 7 days after LI in tamoxifen-treated animals (grey lines) were significantly greater than those in untreated controls (black dashed lines). A-wave amplitudes for both light- and dark-adapted responses in tamoxifen-treated animals were statistically similar to uninjured controls (p >0.99 for both comparisons), indicating full protection. B-wave amplitudes approached those in uninjured controls but did not reach full protection (p<0.05 for both comparisons). (Top row: data points and error bars represent mean and SEM; n=12, 7, and 7 animals for uninjured control, untreated control 7 days post-LI, and tamoxifen treated animals 7 days post-LI respectively. Bottom row: Difference in column means between the 3 groups, all comparison made with 2-way ANOVA, error bars indicate 95% confidence intervals (CI)).

FIGS. 2A-2I. Tamoxifen administration reduced microglial activation and infiltration induced by acute light injury. (A) In vivo fundus autofluorescence (FAF) imaging following light injury revealed the emergence of a punctate hyperautofluorescent pattern centered in the superotemporal quandrant at the level of the subretinal space that peaked in intensity at 7 days post-LI; this pattern of fundus autofluorescence was not observed in tamoxifen-treated animals across the same time-points post-LI. (B) Immunohistochemical analysis of RPE flat-mounts in control animals 14 days post-LI demonstrated that the subretinal hyperautofluorescent spots observed in FAF imaging in vivo and on histological analysis corresponded to Iba1-immunopositive microglia, indicating that microglial infiltration into the outer retina was induced by LI. (C) Histological analysis of retinal sections from experimental animals following LI showed early (1 day post-LI) infiltration of the ONL by Iba1-positive microglia by microglia from the inner retina; this occurred concurrently with the emergence of TUNEL staining in the ONL. Microglia infiltration increased at subsequent time-points with additional accumulation of Iba1+ cells in the subretinal space (arrow). In comparison, microglia infiltration into the outer retina was markedly decreased by tamoxifen treatment. (D) Infiltrating microglia in the outer retina showed expression of the activation marker, CD68 in untreated control animals, which were largely absent in tamoxifen-treated animals. (E,F) Quantitative histological analyses showed the time course of photoreceptor atrophy (as revealed by ONL thinning) (E) and photoreceptor apoptosis (as revealed by TUNEL staining) (F) in control animals, which were both markedly reduced in tamoxifen-treated animals. Morphological rescue of photoreceptors in tamoxifen-treated animals was correlated with decreases in the numbers of infiltrating microglia in the ONL (G) and subretinal space (H), and activated CD68-immunopositive microglia (I). (n=3-5 animals per time point in control and treated groups, p values correspond to comparisons between control and treated groups, 2-way ANOVA).

FIGS. 5A-5G. In vivo mouse model of acute light exposure-induced photoreceptor injury involves photoreceptor apoptosis, retinal atrophy, and loss of photoreceptor cell function. Young adult 2-3 month-old C57B16J mice were dark-reared for 1 week before subjected to pupillary dilation and exposure to ambient white light at $20\times10^3$ lux for 2 h. The effects on retinal structure and function were evaluated at time points from 2 h to 14 days post light injury (LI). (A,B) Retinal thickness and lamination was evaluated in vivo using optical coherence tomography (OCT); 1.4 mm wide scan fields centered on the optic nerve were obtained. Heat-maps (A) representing total retinal thickness of OCT images taken at baseline (before LI) and 7 days post LI demonstrated retinal thinning that was most marked in the superior temporal retina. Individual OCT B-scans from the superior temporal retina (B) show progressive thinning of the outer nuclear layer (ONL) from 3 days post-LI. (C-E) Histological analysis of retina in the superotemporal quadrant (1.25 mm from the optic nerve) revealed prominent emergence of apoptotic photoreceptors (as marked by TUNEL, red) in the ONL starting at 1 day post-LI. Significant thinning of the ONL was observed starting at 3 days post-LI. Plots in D, E show the time course of changes in the density of TUNEL-positive photoreceptors and ONL thickness following LI (column heights and error bars represent mean and SEM; n=3-4 animals per time-point). (F,G) Representative electroretinography (ERG) recordings demonstrating functional decreases at 7 days post-LI relative to uninjured control mice for a- and b-wave amplitudes in dark- and light-adapted responses.

DETAILED DESCRIPTION OF SEVERAL EMBODIMENTS

Figure 1B:
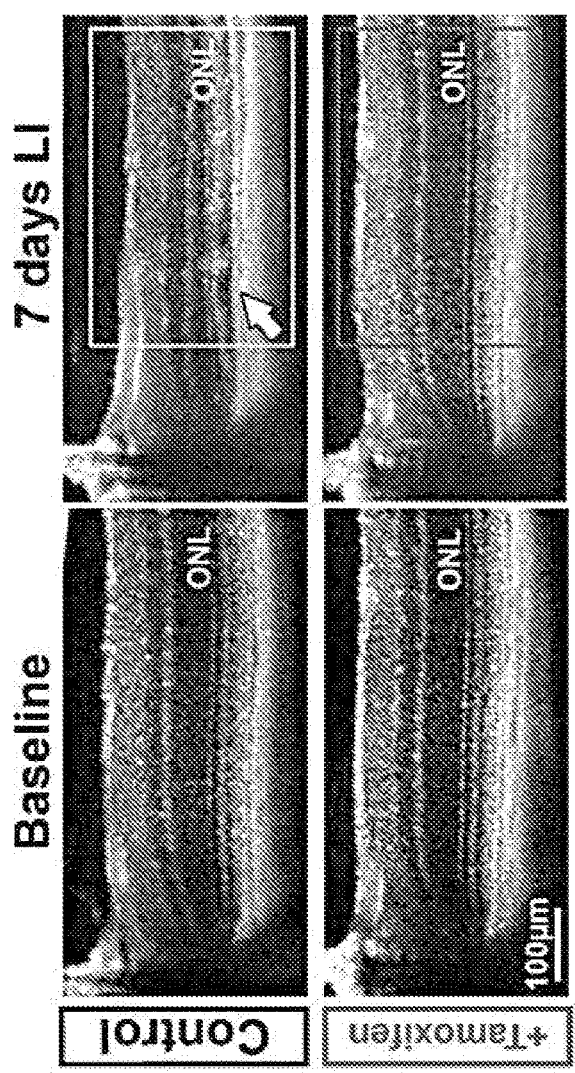

Although tamoxifen previously was clinically associated with a low frequency occurrence of adverse retinal changes, it is disclosed herein that actually exerts broad neuroprotective effects in patients with ongoing photoreceptor degeneration. It was demonstrated that oral administration of SERMS, such as tamoxifen and raloxifene, can be used to treat or prevent retinal degeneration at a variety of dosages.

Methods for treating or preventing retinal degeneration is a subject are disclosed herein. These methods include administering to the subject a therapeutically effective amount of a selective estrogen receptor modulator (SERM) to treat the retinal degeneration in the subject, wherein the SERM is one or more of tamoxifen, afimoxifene, raloxifene, bazedoxifene, arzoxifene, desmethylarzoxifene, or a salt or derivative thereof. In some embodiments, the SERM is a) tamoxifen or a salt or derivative thereof; or b) raloxifene or a salt or derivative thereof. In additional embodiments, the subject is human. In further embodiments, the subject has retinitis pigmentosa, acute retinal degeneration, atrophic macular degeneration, or diabetic retinopathy. In other embodiments, the SERM is administered orally. In some embodiments, the subject does not have cancer, such as breast cancer.

In specific non-limiting examples, the SERM is tamoxifen, or a salt or derivative thereof, the subject is human, and the tamoxifen is administered at a dose of about 0.8 mg/kg to about 6.5 mg/kg daily (≈10 mg/kg/day, approximately equivalent to a 0.81 mg/kg/day dose in an adult human). In other non-limiting examples, the SERM is tamoxifen, or a salt or derivative thereof, the subject is human, and the tamoxifen is administered orally at a dose of about 3.2 mg/kg to about 6.5 mg per kg daily. In yet other embodiments, the SERM is administered for a minimum of three months. In more embodiments, the SERM defers photoreceptor loss, reduces photoreceptor function decrement, reduces visual function loss, suppresses retinal microglial activation and/or suppresses pro-inflammatory cytokine expression.

In some embodiments, the methods include evaluating the vision of the subject. In one specific non-limiting examples, the methods include performing electroretinography on the subject.

Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GENBANK® Accession Nos. referred to herein are the sequences available at least as early as Aug. 19, 2016. All references, patent applications and publications, and GENBANK® Accession numbers cited herein are incorporated by reference. In order to facilitate review of the various embodiments of the disclosure, the following explanations of specific terms are provided:

Age-related macular degeneration (AMD): A disease that is a major cause of blindness in the United States and other industrialized nations. (Evans J, Wormald R., British Journal Ophthalmology 80:9-14, 1996; Klein R, Klein B E K, Linton K L P, Ophthalmology 99:933-943, 1992; Vingerling J R, Ophthalmology 102:205-210, 1995). Early AMD is characterized clinically by drusen, which are extracellular deposits of proteins, lipids, and cellular debris, (Hageman G S, Mullins R F, Mol Vis 5:28, 1999), that are located beneath the retinal pigment epithelium (RPE). The RPE provides nutritional, metabolic, and phagocytic functions for the overlying photoreceptors. Significant vision loss results from dysfunction or death of photoreceptors in the macula in association with late stages of AMD (geographic atrophy of the retinal pigment epithelial cells and subretinal neovascularization).

Animal: Living multi-cellular vertebrate organisms, a category that includes, for example, mammals and birds. The term mammal includes both human and non-human mammals. Similarly, the term "subject" includes both human and veterinary subjects.

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV).

Breast carcinomas lose the typical histology and architecture of normal breast glands. Generally, carcinoma cells overgrow the normal cells and lose their ability to differentiate into glandular like structures. The degree of loss of differentiation in general is related to the aggressiveness of the tumor. For example, "in situ" carcinoma by definition retains the basement membrane intact, whereas as it progresses to "invasive", the tumor shows breakout of basement membranes. Thus one would not expect to see, within breast carcinomas, staining of a discrete layer of basal cells as seen in normal breast tissue. For a discussion of the physiology and histology of normal breast and breast carcinoma, see Ronnov-Jessen, L., Petersen, O. W. & Bissell, M. J. Cellular changes involved in conversion of normal to malignant breast: importance of the stromal reaction (see, for example, Physiol Rev 76, 69-125, 1996).

Breast cancers can be divided into groups based on their expression profiles. Basal-type carcinomas usually are negative for expression of estrogen receptor (ER) and negative for expression of HER2 (erbB2) and progesterone receptor (PR), and thus are referred to as "triple-negative breast cancers" or "TNBC." This type of breast cancer is also denoted $ER^-/HER2^-/PR^-$ and represents about 15-20% of all breast cancer, and generally cannot be treated using Her2 targeted or estrogen targeted therapies. It is believed that the aggressive nature of this cancer is correlated with an enrichment for cancer stem cells (CSC) with a $CD44^+CD24^{-/lo}$ phenotype. In some embodiments, basal carcinomas are negative for expression of progesterone receptor (PR), positive for expression of epidermal growth factor receptor (EGFR), and positive for expression of cytokeratin 5 (CK5). This phenotype is denoted as follows: $ER^-/PR^-/HER2^-/CK5^+/EGFR^+$.

Cell Culture: Cells grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Leber congenital amaurosis (LCA): A rare inherited eye disease that appears at birth or in the first few months of life and primarily affects the retina. The presentation can vary because is it associated with multiple genes. However, it is characterized by characterized by nystagmus, photophobia, sluggish or absent pupillary response, and severe vision loss or blindness.

The pupils, which usually expand and contract in response to the amount of light entering the eye, do not react normally to light. Instead, they expand and contract more slowly than normal, or they may not respond to light at all. Additionally, the clear front covering of the eye (the cornea) may be cone-shaped and abnormally thin, a condition known as keratoconus.

A specific behavior called Franceschetti's oculo-digital sign is characteristic of Leber congenital amaurosis. This sign consists of poking, pressing, and rubbing the eyes with a knuckle or finger.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the SERMS herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Photic Retinopathy: Damage to the retina, such as the macula, from prolonged exposure to solar radiation or other bright light, e.g. lasers or arc welders. The term includes solar, laser, and welder's retinopathy. In some embodiments, photic retinopathy is caused by intense artificial light or sunlight. The light can be ultraviolet light (UV-B, 295-320 nm; UV-A, 320-400 nm) or visible light (400-700 nm). Phototoxic damage can occur in retinal pigment epithelial cells, the choroid, and the rod outer segments. Photic retinopathy results in reduced visual acuity in the long-term, and central or paracentral scotoma. Fundus changes are usually (but not always) bilateral Phototoxicity: Damage to cells, such as damage to cells of the retina, induced by light.

Preventing or treating a disease: "Preventing" a disease refers to inhibiting the full development of a disease, for example in a person who is known to have a predisposition to a disease such as age related macular degeneration. An example of a person with a known predisposition is someone with a history of a disease in the family, or who has been exposed to factors that predispose the subject to a condition. "Treatment" refers to a therapeutic intervention that ameliorates a sign or symptom of a disease or pathological condition after it has begun to develop.

Retina: The light (photon) sensitive portion of the eye, that contains the photoreceptors (cones and rods) for light. Rods and cones perform light perception through the use of light sensitive pigments. The light sensitive pigments are made of protein called opsin and a chromophore called retinene, which the variant is of vitamin A. The rods contain rhodopsin while the cones contains iodopsin. Rods and cones transmit signals through successive neurons that trigger a neural discharge in the output cells of the retina and the ganglion cells. The visual signals are conveyed by the optic nerve to the lateral geniculate bodies from where the visual signal is passed to the visual cortex (occipital lobe) and registered as a visual stimulus. "Rod cells", or "rods," are photoreceptor cells in the retina of the eye that can function in less intense light than the other type of visual photoreceptor, cone cells. Rods are concentrated at the outer edges of the retina and are used in peripheral vision. Rods are a little longer and leaner than cones but have the same structural basis. The opsin or pigment is on the outer side, lying on the retinal pigment epithelium, completing the cell's homeostasis. This epithelium end contains many stacked disks. Rods have a high area for visual pigment and thus substantial efficiency of light absorption. Like cones, rod cells have a synaptic terminal, an inner segment, and an outer segment. The synaptic terminal forms a synapse with another neuron, for example a bipolar cell. The inner and outer segments are connected by a cilium, which lines the distal segment. The inner segment contains organelles and the cell's nucleus, while the rod outer segment, which is pointed toward the back of the eye, contains the light-absorbing materials. Activation of photopigments by light sends a signal by hyperpolarizing the rod cell, leading to the rod cell not sending its neurotransmitter, which leads to the bipolar cell then releasing its transmitter at the bipolar-ganglion synapse and exciting the synapse. "Cone cells," or "cones," are responsible for color vision and function best in relatively bright light. Cone cells are densely packed in the fovea centralis, a 0.3 mm diameter rod-free area with very thin, densely packed cones which quickly reduce in number towards the periphery of the retina. There are about six to seven million cones in a human eye and are most concentrated towards the macula. Cones are less sensitive to light than the rod cells in the retina (which support vision at low light levels), but allow the perception of color. They are also able to perceive finer detail and more rapid changes in images, because their response times to stimuli are faster than those of rods. In humans, cones are normally one of the three types, each with different pigment, namely: S-cones, M-cones and L-cones. Each cone is therefore sensitive to visible wavelengths of light that correspond to short-wavelength, medium-wavelength and long-wavelength light. The three types have peak wavelengths near 420-440 nm, 534-545 nm and 564-580 nm, respectively, depending on the individual.

Retinal Pigment Epithelium: The pigmented layer of hexagonal cells, present in vivo in mammals, just outside of the neurosensory retinal that is attached to the underlying choroid. These cells are densely packed with pigment granules, and shield the retinal from incoming light. The retinal pigment epithelium also serves as the limiting transport factor that maintains the retinal environment by supplying small molecules such as amino acid, ascorbic acid and D-glucose while remaining a tight barrier to choroidal blood borne substances.

Retinitis pigmentosa (RP): An inherited, degenerative eye disease that causes severe vision impairment due to the progressive degeneration of the rod photoreceptor cells in the retina. This form of retinal dystrophy manifests initial symptoms independent of age. The initial retinal degenerative symptoms of Retinitis pigmentosa are characterized by decreased night vision (nyctalopia) and the loss of the mid-peripheral visual field. The rod photoreceptor cells, which are responsible for low-light vision and are orientated in the retinal periphery, are the retinal processes affected first during non-syndromic forms of this disease. Visual decline progresses relatively quickly to the far peripheral field, eventually extending into the central visual field as tunnel vision increases. Visual acuity and color vision can become compromised due to accompanying abnormalities in the cone photoreceptor cells, which are responsible for color vision, visual acuity, and sight in the central visual field. The progression of disease symptoms occurs in a symmetrical manner, with both the left and right eyes experiencing symptoms at a similar rate. There are multiple genes that, when mutated, can cause the retinitis pigmentosa phenotype.

Inheritance patterns of RP have been identified as autosomal dominant, autosomal recessive, X-linked, and maternally (mitochondrially) acquired, and are dependent on the specific RP gene mutations present in the parental generation.

Selection Estrogen Receptor Modulator (SERM): A class of agents that act on the estrogen receptor. A characteristic that distinguishes these substances from estrogen receptor agonists and antagonists is that their action is different in various tissues, thereby granting the possibility to selectively inhibit or stimulate estrogen-like action in various tissues. In general, SERMs are competitive partial agonists of the ER. Different tissues have different degrees of sensitivity to and activity of endogenous estrogens, so SERMs produce estrogenic or antiestrogenic effects depending on the specific tissue in question as well as the percentage of intrinsic activity (IA) of the SERM. An example of a SERM with high IA and thus mostly estrogenic effects is chlorotrianisene, while an example of a SERM with low IA and thus mostly antiestrogenic effects is ethamoxytriphetol. SERMs like clomifene and tamoxifen are more in the middle in their IA and their balance of estrogenic and antiestrogenic actions in comparison. Raloxifene is a SERM that is more antiestrogenic than tamoxifen; both are estrogenic in bone, but raloxifene is antiestrogenic in the uterus while tamoxifen is estrogenic.

Subject: Human and non-human animals, including all vertebrates, such as mammals and non-mammals, such as non-human primates, mice, rabbits, sheep, dogs, cats, horses, cows, chickens, amphibians, and reptiles. In many embodiments of the described methods, the subject is a human. Therapeutic agent: Used in a generic sense, it includes treating agents, prophylactic agents, and replacement agents. A SERM is one form of a therapeutic agent.

Therapeutically effective amount: A quantity of an agent sufficient to achieve a desired effect in a subject being treated. For instance, this can be the amount of a SERM to treat or prevent retinal degeneration in a subject, or a dose sufficient to prevent advancement, or to treat retinal degeneration. In one example, the amount is sufficient to prevent advancement, or to cause regression of the disease. In another example, the amount inhibits progression of retinal degeneration. A therapeutically effective amount of a SERM, such as tamoxifen or a salt or derivative thereof, used to achieve a specific desired effect on a biological process, such as to reduce or inhibit degeneration of the retina, can be different than the dose of same compound that results in an effect on a different biological process, such as killing cancer cells.

A therapeutically effective amount of a SERM can be administered systemically or locally (see below). In addition, an effective amount of a SERM can be administered in a single dose, or in several doses, for example daily, during a course of treatment. However, the effective amount of the SERM will be dependent on the preparation applied, the subject being treated, the severity and type of the affliction, and the manner of administration of the compound.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or improving vision. The treatment may be assessed by objective or subjective parameters; including the results of a physical examination, neurological examination, or psychiatric evaluations.

Tumor and Cancer: A tumor is an abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma).

Uveitus: An intraocular inflammatory disease that includes iritis, cyclitis, panuveits, posterior uveitis and anterior uveitis. Iritis is inflammation of the iris. Cyclitis is inflammation of the ciliary body. Panuveitis refers to inflammation of the entire uveal (vascular) layer of the eye. Intermediate uveitis, also called peripheral uveitis, is centered in the area immediately behind the iris and lens in the region of the ciliary body and pars plana, and is also termed "cyclitis" and "pars planitis."

"Posterior" uveitis generally refers to chorioretinitis (inflammation of the choroid and retina). Posterior uveitis can give rise to diverse symptoms but most commonly causes floaters and decreased vision similar to intermediate uveitis. Signs include cells in the vitreous humor, white or yellow-white lesions in the retina and/or underlying choroid, exudative retinal detachments, retinal vasculitis, and optic nerve edema.

Anterior uveitis refers to iridocyclitis (inflammation of the iris and the ciliary body) and/or iritis. Anterior uveitis tends to be the most symptomatic, typically presenting with pain, redness, photophobia, and decreased vision. Signs of anterior uveitis include pupillary miosis and injections of the conjunctiva adjacent to the cornea, so-called perilimbal flush. Biomicroscopic, or slit lamp, findings include cells and flare in the aqueous humor as well as keratic precipitates, which are clumps of cells and proteinaceous material adherent to the corneal endothelium. "Diffuse" uveitis implies inflammation involving all parts of the eye, including anterior, intermediate, and posterior structures.

"Acute" uveitis is a form of uveitis in which signs and symptoms occur suddenly and last for up to about six weeks. "Chronic" uveitis is a form in which onset is gradual and lasts longer than about six weeks.

The inflammatory products (i.e., cells, fibrin, excess proteins) of ocular inflammation are commonly found in the fluid spaces of the eye, i.e., anterior chamber, posterior chamber and vitreous space as well as infiltrating the tissue imminently involved in the inflammatory response.

The subject can have uveitis. Uveitis may occur following surgical or traumatic injury to the eye; as a component of an autoimmune disorder (such as rheumatoid arthritis, Bechet's disease, ankylosing spondylitis, sarcoidosis), as an isolated immune mediated ocular disorder (such as pars planitis or iridocyclitis), as a disease unassociated with known etiologies, and following certain systemic diseases which cause antibody-antigen complexes to be deposited in the uveal tissues. Uveitis includes ocular inflammation associated with Bechet's disease, sarcoidosis, Vogt-Koyanagi-Harada syndrome, birdshot chorioretinopathy and sympathetic ophthalmia. Thus, non-infectious uveitis occurs in the absence of an infectious agent.

A wide variety of infective agents can also cause uveitis. When an infective etiology has been diagnosed, an appropriate antimicrobial drug can be given to cure the disease. However, the etiology of uveitis remains elusive in the majority of cases.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

SERMS and Pharmaceutical Compositions

Tamoxifen is the trans isomer of 1-(p-beta-dimethyaminoetho-xyphenyl)-1,2-diphenylbut-1-ene, which is disclosed in U.S. Pat. No. 4,536,516, incorporated herein by reference. An alternative name is (Z)-2-[p-(1,2-diphenylbut-1-enyl)pheno-xy]ethyldimethylamine. The structure of tamoxifen is shown below.

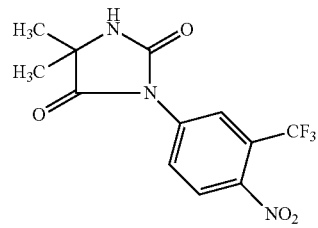 [SMILES: CC1(C)NC(=O)N(c2ccc([N+](=O)[O-])c(C(F)(F)F)c2)C1=O]

Tamoxifen, and pharmaceutically acceptable salts and solvates thereof are known to be useful in the treatment of hormone-dependent tumors, such as for the treatment of breast cancer in women, see U.S. Patent Application Publication No. 2003/0158160. Reviews of its clinical usage are available, for example by Purr and Jordan in "Pharmacology and Therapeutics", 1984, Volume 25, pages 127-205. Pharmaceutically acceptable salts of tamoxifen are known. A suitable pharmaceutically acceptable acid-addition salt is, for example, the hydrochloride, hydrobromide, citrate or D-gluconate salt. Tamoxifen is marketed under the tradename NOLVADEX®.

Tamoxifen, or a salt (also called a "pharmaceutically acceptable salt") or derivative thereof, is an "anti-estrogen," a selective estrogen-receptor modulator. Anti-estrogens such as tamoxifen have been shown to dramatically reduce the risk of breast cancer (Powles, T. J., Nat Rev Cancer, 2:787-794, 2002) and of breast cancer recurrence (Jordan, V. C., Nat Rev Drug Discov, 2:205-213, 2003). Tamoxifen is a partial agonist and exhibits both species and tissue specificity for inducing either an agonist or antagonist response. In both rats and humans, tamoxifen exhibits partial agonism, e.g., producing antagonist effects in the breast, but agonist effects in the vagina and endometrium. Long-term tamoxifen use has been associated with a reduced incidence of contralateral breast cancer (antagonist), a reduced incidence of primary breast cancer in high-risk women (antagonist), maintenance of bone density (agonist), and increased risk of endometrial carcinomas (agonist). At doses used to treat breast cancer, tamoxifen has been associated with retinopathy. The present disclosure is related to the use of tamoxifen, and salts and derivatives thereof, for the treatment or prevention of retinal degeneration.

Derivatives of tamoxifen are known in the art, see for example, U.S. Patent Application Publication No. 2016/0075726, U.S. Patent Application Publication No. 2006/0105041 and U.S. Patent Application Publication No. 2004/0138314, which are incorporated herein by reference. U.S. Pat. No. 5,219,549, incorporated herein by reference, discloses tamoxifen derivatives wherein the alkyl chain of the molecule is substituted with fluorine or iodine, such as fluorotamoxifen. The compound 4-hydroxy tamoxifen (afimoxifene), or 1-[4-(2-N-dimethylaminoethoxy)-phenyl]-1-(4-hydroxyphenyl)-2-phenylbut-1-(Z)-ene, constitutes an active metabolite of the well characterized anti-estrogen compound, tamoxifen. Both cis and trans isomers exist, either of which, alone or in combination, are useful. Methods for preparing 4-hydroxy tamoxifen are well known. For example, U.S. Pat. No. 4,919,937, incorporated herein by reference, discloses a synthesis derived methods that occurs in several stages: Stage 1—Reaction between 4-(β-dimethylaminoethoxy)-α-ethyldeoxybenzoin and p-(2-tetrahydropyranyloxy)phenylmagnesium bromide; Stage 2—Separately from stage 1, formation of 1-(4-hydroxyphenyl)-2-phenyl-1-butanone by hydroxylation of 1,2-diphenyl-1-butanone; Stage 3—Reaction between the products of stages 1 and 2 to form 1-(4-dimethylaminoethoxyphenyl)-[4p-2-tetrahydropyranyloxy)phenyl]-2-phe-nylbutan-1-ol; Stage 4—Dehydration with methanol/hydrochloric acid produces 1-[p-(β-dimethylaminoethoxy)phenyl]-trans-1-(p-hydroxy-pheny-1)-2-pheny-1-but-1-ene=4-OH-tamoxifen, a mixture of cis and trans isomers; Stage 5—Separation of the cis and trans isomers by chromatography and crystallization to constant specific activity. Suitable doses are disclosed for example, in U.S. Pat. No. 7,485,623, which is incorporated herein by reference.

Raloxifene ([6-hydroxy-2-(4-hydroxyphenyl)-benzothi-ophen-3-yl]-[4-[2-(1-piperidyl)ethoxy]phenyl]-methanone), shown below, is also of use in the methods disclosed herein. The structure of raloxifene is shown below:

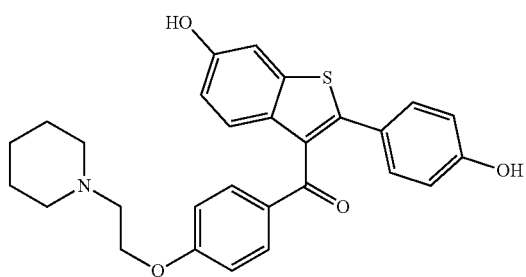 [SMILES: O=C(c1ccc(OCCN2CCCCC2)cc1)c1c(-c2ccc(O)cc2)sc2cc(O)ccc12]

Bazedoxifene (1-{4-[2-(Azepan-1-yl)ethoxy]benzyl}-2-(4-hydroxyphenyl)-3-methyl-1H-indol-5-ol) is a third generation SERM developed by Pfizer; the structure is shown below:

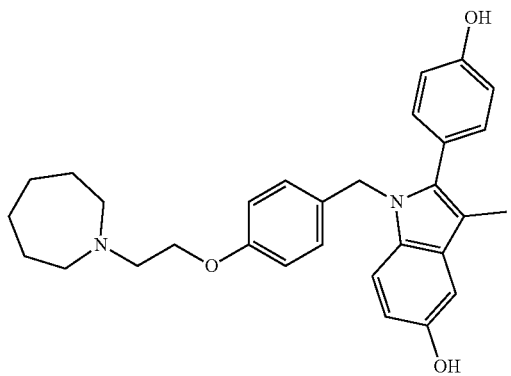 [SMILES: Cc1c(-c2ccc(O)cc2)n(Cc2ccc(OCCN3CCCCCC3)cc2)c2ccc(O)cc12]

Bazedoxifene has been approved for use in postmenopausal osteoporosis, and has been used for treatment of dyspareunia, breast cancer, and pancreatic cancer. Bazedoxifene is also of use in the methods disclosed herein.

Arzoxifene (2-(4-Methoxyphenyl)-3-[4-(2-piperidin-1-ylethoxy)phenyl]-1-benzothiophen-6-ol) is a SERM that is a potent estrogen antagonist in mammary and uterine tissue while acting as an estrogen agonist to maintain bone density and lower serum cholesterol. Arzoxifene is also of use in the methods disclosed herein. The structure of arzoxifene is shown below:

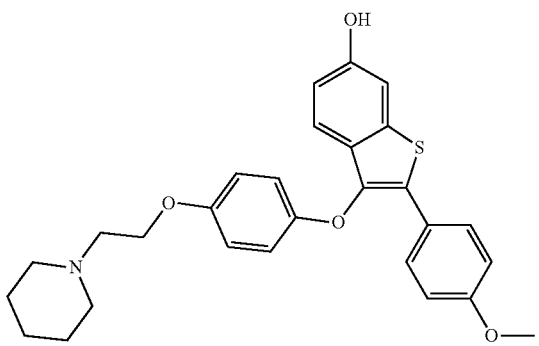 [SMILES: COc1ccc(-c2sc3cc(O)ccc3c2Oc2ccc(OCCN3CCCCC3)cc2)cc1]

Desmethylarzoxifene (2-(4-hydroxyphenyl)-3-[4-(2-piperidin-1-ylethoxy)phenoxy]-1-benzothiophen-6-ol) is also a SERM and is of use in the methods disclosed herein. Desmethylarzoxifene blocks estrogen-induced malignant transformation of human breast epithelial cell lines (Kastrati et al., PLOS One 6(11): e27876, 2011). The structure of desmethylarzoxifene is shown below:

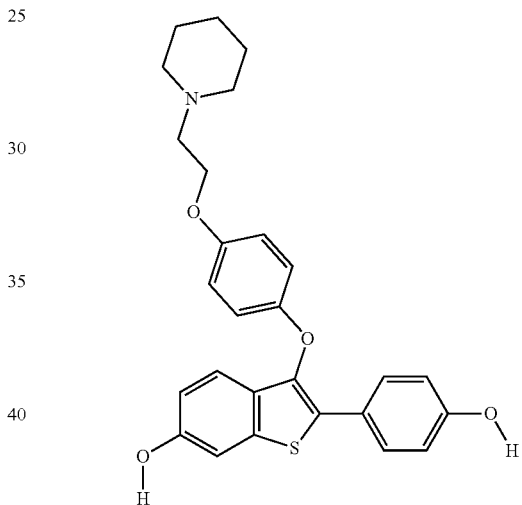

Thus, in some embodiments, the methods include administering a therapeutically effective amount of raloxifene, bazedoxifene, arzoxifene, desmethylarzoxifene, tamoxifen and/or a pharmaceutically acceptable salt or derivative thereof.

Pharmaceutical compositions are thus provided for both local use (for example, topical or within an ocular transplant), as well as for systemic use. The subject can be any subject, such as a mammalian subject. Therefore, the disclosure includes within its scope pharmaceutical compositions comprising a SERM, raloxifene, bazedoxifene, arzoxifene, desmethylarzoxifene, tamoxifen and/or a pharmaceutically acceptable salt or derivative thereof, formulated for use in human or veterinary medicine. In one embodiment, the SERM, such as SERM, raloxifene, bazedoxifene, arzoxifene, desmethylarzoxifene, tamoxifen and/or a pharmaceutically acceptable salt or derivative thereof, is formulated for oral administration.

Pharmaceutical compositions that include a SERM, such as raloxifene, bazedoxifene, arzoxifene, desmethylarzoxifene, tamoxifen and/or a pharmaceutically acceptable salt or derivative thereof, can be formulated with an appropriate solid or liquid carrier, depending upon the particular mode of administration chosen. For oral administration, the SERM, such as raloxifene, bazedoxifene, arzoxifene, desmethylarzoxifene, tamoxifen and/or a pharmaceutically acceptable salt or derivative thereof, can be formulated for any particular route of administration. For oral administration, flavorings, colors and sweeteners can be added. Oral formulations may be liquid (e.g., syrups, solutions, or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

The pharmaceutical compositions can contain the SERM and a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

The amount of the various excipients present in any of the disclosed compositions varies and is readily determined by one of skill in the art. For example, a protein excipient, such as BSA, if present, will can be present at a concentration of between 1.0 weight (wt.) % to about 20 wt. %, such as 10 wt. %. If an amino acid such as glycine is used in the formulations, it can be present at a concentration of about 1 wt. % to about 5 wt. %. A carbohydrate, such as sorbitol, if present, can be present at a concentration of about 0.1 wt % to about 10 wt. %, such as between about 0.5 wt. % to about 15 wt. %, or about 1 wt. % to about 5 wt. %. If polyethylene glycol is present, it can generally be present on the order of about 2 wt. % to about 40 wt. %, such as about 10 wt. % top about 25 wt. %. If propylene glycol is used in the subject formulations, it will typically be present at a concentration of about 2 wt. % to about 60 wt. %, such as about 5 wt. % to about 30 wt. %. If a detergent such as a sorbitan ester (TWEEN®) is present, it can be present at a concentration of about 0.05 wt. % to about 5 wt. %, such as between about 0.1 wt. % and about 1 wt %, see U.S. Published Patent Application No. 2012/0219528, which is incorporated herein by reference.

The dosage form of the pharmaceutical composition will be determined by the mode of administration chosen. For instance, topical and oral formulations can be employed.

The pharmaceutical compositions that include a SERM, such as raloxifene, bazedoxifene, arzoxifene, desmethylarzoxifene, tamoxifen and/or a pharmaceutically acceptable salt or derivative thereof, in some embodiments, can be formulated in unit dosage form, suitable for individual administration of precise dosages. The amount of active compound(s) administered will be dependent on the subject being treated, the severity of the affliction, and the manner of administration, and can be left to the judgment of the prescribing clinician. Within these bounds, the formulation to be administered will contain a quantity of the active component(s) in amounts effective to achieve the desired effect in the subject being treated, such as treatment or prevention of retinal degeneration. The effect can also be on microglia, or a particular ocular motor response. The SERM can be formulated with additional therapeutic agents.

In some embodiments, the SERM is formulated for delivery to the eye. Topical preparations can include eye drops, ointments, sprays and the like. Eye drops or sprays can be provided in unit dose dispensers (such as eye drop bottles that dispense a metered unit dose that contains the SERM, such as raloxifene, bazedoxifene, arzoxifene, desmethylarzoxifene, tamoxifen and/or a pharmaceutically acceptable salt or derivative thereof, either alone or in combination with other therapeutic agents).

The SERM can be included in an inert matrix for either topical application or injection into the eye, such as for intra-vitreal administration. As one example of an inert matrix, liposomes may be prepared from dipalmitoyl phosphatidylcholine (DPPC), such as egg phosphatidylcholine (PC). Liposomes, including cationic and anionic liposomes, can be made using standard procedures as known to one skilled in the art. Liposomes including a SERM can be applied topically, either in the form of drops or as an aqueous based cream, or can be injected intraocularly. In a formulation for topical application, the SERM is slowly released over time as the liposome capsule degrades due to wear and tear from the eye surface. In a formulation for intraocular injection, the liposome capsule degrades due to cellular digestion. Both of these formulations provide advantages of a slow release drug delivery system, allowing the subject to be exposed to a substantially constant concentration of the SERM over time. In one example, the SERM can be dissolved in an organic solvent such as DMSO or alcohol as previously described and contain a polyanhydride, poly (glycolic) acid, poly(lactic) acid, or polycaprolactone polymer.

The SERM, such as raloxifene, bazedoxifene, arzoxifene, desmethylarzoxifene, tamoxifen and/or a pharmaceutically acceptable salt or derivative thereof, can be included in a delivery system that can be implanted or injected at various sites in and around the eye, depending on the size, shape and formulation of the implant or injection. The SERM can be used alone. However, in another embodiment, at least one additional agent, such as at least one agent that is described above, can be included along with the SERM in the delivery system, such as in an implant. The delivery system is then introduced into the eye. Suitable sites include but are not limited to the anterior chamber, anterior segment, posterior chamber, posterior segment, vitreous cavity, suprachoroidal space, subconjunctiva, episcleral, intracorneal, epicorneal and sclera. In one example, the SERM delivery system is placed in the anterior chamber of the eye. In another example, the SERM delivery system is placed in the vitreous cavity.

The implants can be inserted into the eye by a variety of methods, including placement by forceps or by trocar following making an incision in the sclera (for example, a 2-3 mm incision) or other suitable site. In some cases, the implant can be placed by trocar without making a separate incision, but instead by forming a hole directly into the eye with the trocar. The method of placement can influence the release kinetics. For example, implanting the device into the vitreous or the posterior chamber with a trocar may result in placement of the device deeper within the vitreous than placement by forceps, which may result in the implant being closer to the edge of the vitreous. The location of the implanted device may influence the concentration gradients of SERM surrounding the device, and thus influence the release rates (for example, a device placed closer to the edge of the vitreous may result in a slower release rate, see U.S. Pat. Nos. 5,869,079 and 6,699,493).

The SERM is delivered to the eye for a sufficient time period to achieve the desired effect. Thus, in one embodiment, the SERM is delivered for at least about 2 days, such as for about five days, seven days, ten days, 14 or 21 days. In several embodiments, the immunosuppressive agent is delivered for at least about one week, at least about two weeks, at least about three weeks, at least about four weeks, at least about five weeks, at least about six weeks, at least about seven weeks, at least about eight weeks, at least about nine weeks, at least about 10 weeks, and at least about 12 weeks. In one embodiment, extended periods of delivery are achieved with the use of an implant. The duration of use of a SERM can be the medical history of the patient and other contributing factors (such as use of other agents, etc.). If extended periods of administration are required, the SERM can be administered for up to six months, or one year, two years, three years, or longer. In one embodiment, for extended release, an implant is utilized. More than one implant can also be utilized. For example, implants can be sequentially implanted into the vitreous in order to maintain concentrations for even long periods. In one embodiment, more than one implant can be sequentially implanted into the eye in order to maintain therapeutic drug concentrations for longer periods.

The use of implants is well known in the art (see U.S. Pat. Nos. 6,699,493 and 5,869,079). In one embodiment, an implant is formulated with the SERM associated with a bioerodible polymer matrix.

Generally, when implants are used, the SERM is homogeneously distributed through the polymeric matrix, such that it is distributed evenly enough that no detrimental fluctuations in rate of release occur because of uneven distribution of the agent in the polymer matrix. The selection of the polymeric composition to be employed varies with the desired release kinetics, the location of the implant, patient tolerance, and the nature of the implant procedure. The polymer can be included as at least about 10 weight percent of the implant. In one example, the polymer is included as at least about 20 weight percent of the implant. In another embodiment, the implant comprises more than one polymer. These factors are described in detail in U.S. Pat. No. 6,699,493. Characteristics of the polymers generally include biodegradability at the site of implantation, compatibility with the agent of interest, ease of encapsulation, and water insolubility, amongst others. Generally, the polymeric matrix is not fully degraded until the drug load has been released. The chemical composition of suitable polymers is known in the art (for example, see U.S. Pat. No. 6,699,493).

For delivery to the eye, the SERM, such as raloxifene, bazedoxifene, arzoxifene, desmethylarzoxifene, tamoxifen and/or a pharmaceutically acceptable salt or derivative thereof, can be formulated in an implantable form with other carriers and solvents. For example, buffering agents and preservatives can be employed. Water soluble preservatives include sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. These agents can be present in individual amounts of from about 0.001 to about 5% by weight, such as about 0.01 to about 2%. Suitable water soluble buffering agents that may be employed are sodium carbonate, sodium borate, sodium phosphate, sodium acetate, sodium bicarbonate. These agents can be present in amounts sufficient to maintain a pH of the system of between about 2 to about 9 such as about 4 to about 8, or at about 6 to about 7. In one example, the pH of the system is maintained at about 7. As such, the buffering agent can be as much as 5% on a weight-to-weight basis of the total composition. Electrolytes such as sodium chloride and potassium chloride may also be included in the formulation. The proportions of SERM, polymer, and any other modifiers may be empirically determined by formulating several implants with varying proportions. A USP approved method for dissolution or release test can be used to measure the rate of release (USP 23; NF 18 (1995) pp. 1790-1798). The implant sizes and shape can also be varied for use in particular regions of the eye (see U.S. Pat. No. 5,869,079).

The SERM can be formulated with additional therapeutic agents. Exemplary agents include cyclosporine, FK506, steroids such as hydrocortisone, antibodies (such as anti-CD4 or antibodies that specifically bind the IL-2 receptor), cytokines (such as beta-interferon), or non-steroidal anti-inflammatory agents. Additional agents include antibacterial antibiotics, such as minoglycosides (for example, amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (for example, azidamfenicol, chloramphenicol, florfenicol, thiamphenicol), ansamycins (for example, rifamide, rifampin, rifamycin sv, rifapentine, rifaximin), β-lactams (for example, carbacephems (e.g., loracarbef), carbapenems (for example, biapenem, imipenem, meropenem, panipenem), cephalosporins (for example, cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (for example, cefbuperazone, cefmetazole, cefminox, cefotetan, cefoxitin), monobactams (for example, aztreonam, carumonam, tigemonam), oxacephems, flomoxef, moxalactam), penicillins (for example, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin g benzathine, penicillin g benzhydrylamine, penicillin G calcium, penicillin G hydrabamine, penicillin G potassium, penicillin G procaine, penicillin N, penicillin 0, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, ticarcillin), other (for example, ritipenem), lincosamides (for example, clindamycin, lincomycin), macrolides (for example, azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (for example, amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (for example, apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin). Agents of use also include synthetic antibacterials, such as 2,4-Diaminopyrimidines (for example, brodimoprim, tetroxoprim, trimethoprim), nitrofurans (for example, furaltadone, furazolium chloride, nifuradene, nifuratel, nifurfoline, nifurpirinol, nifurprazine, nifurtoinol, nitrofurantoin), quinolones and analogs (for example, cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (for example, acetyl sulfamethoxypyrazine, benzylsulfamide, chloramine-b, chloramine-t, dichloramine t, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (for example, acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (for example, clofoctol, hexedine, methenamine, methenamine anhydromethylene-citrate, methenamine hippurate, methenamine mandelate, methenamine sulfosalicylate, nitroxoline, taurolidine, xibornol).

Additional agents of use include antifungal antibiotics such as polyenes (for example, amphotericin B, candicidin, dennostatin, filipin, fungichromin, hachimycin, hamycin, lucensomycin, mepartricin, natamycin, nystatin, pecilocin, perimycin), others (for example, azaserine, griseofulvin, oligomycins, neomycin undecylenate, pyrrolnitrin, siccanin, tubercidin, viridin) allylamines (for example, butenafine, naftifine, terbinafine), imidazoles (for example, bifonazole, butoconazole, chlordantoin, chlormiidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (for example, tolciclate, tolindate, tolnaftate), triazoles (for example, fluconazole, itraconazole, saperconazole, terconazole) others (for example, acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate). Antineoplastic agents can also be of use including (1) antibiotics and analogs (for example, aclacinomycins, actinomycin, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), (2) antimetabolites such as folic acid analogs (for example, denopterin, edatrexate, methotrexate, piritrexim, pteropterin, Tomudex®, trimetrexate), (3) purine analogs (for example, cladribine, fludarabine, 6-mercaptopurine, thiamiprine, thioguanine), (4) pyrimidine analogs (for example, ancitabine, azacitidine, 6-azauridine, carmofur, cytarabine, doxifluridine, emitefur, enocitabine, floxuridine, fluorouracil, gemcitabine, tagafur).

Steroidal anti-inflammatory agents can also be included such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, cyclosporine, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide. In addition, non-steroidal anti-inflammatory agents can be used. These include aminoarylcarboxylic acid derivatives (for example, enfenamic acid, etofenamate, flufenamic acid, isonixin, meclofenamic acid, mefenamic acid, niflumic acid, talniflumate, terofenamate, tolfenamic acid), arylacetic acid derivatives (for example, aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (for example, bumadizon, butibufen, fenbufen, xenbucin), arylcarboxylic acids (for example, clidanac, ketorolac, tinoridine), arylpropionic acid derivatives (for example, alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (for example, difenamizole, epirizole), pyrazolones (for example, apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (for example, acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (for example, ampiroxicam, droxicam, isoxicam, lornoxicam, piroxicam, tenoxicam), .epsilon.-acetamidocaproic acid, s-adenosylmethionine, 3-amino-4-hydroxybutyric acid, amixetrine, bendazac, benzydamine, .alpha.-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

Methods of Treatment

Methods are disclosed herein for treating and/or preventing retinal degeneration in a subject. The methods can include selecting a subject with retinal degeneration, or a subject that is of risk for retinal degeneration. Generally, the therapeutically effective amount of the SERM, such as, but not limited to, one or more of tamoxifen, afimoxifene, raloxifene, bazedoxifene, arzoxifene, desmethylarzoxifene, or a salt or derivative thereof, is sufficient to treat, inhibit and/or prevent retinal degeneration. In some embodiments, the subject has ongoing photoreceptor degeneration.

In some embodiments, methods are disclosed for treating retinitis pigmentosa, age related macular degeneration or Leber Congenital amaurosis (LCA) in a subject. These methods includes selecting a subject with retinitis pigmentosa, age related macular degeneration, or LCA, and administering to the subject an effective amount of a SERM, such as one or more of tamoxifen, afimoxifene, raloxifene, bazedoxifene, arzoxifene, desmethylarzoxifene, or a salt or derivative thereof, to treat and/or prevent the retinal degeneration in the subject. The method can include selecting a subject with the retinal degeneration, such as retinitis pigmentosa, age-related macular degeneration or LCA.

In some embodiments, the subject does not have a tumor, such as a cancer. In some non-limiting examples, the subject does not have breast cancer. The subject can be male or female. Human and veterinary subjects can be treated using the disclosed methods.

The subject can have ocular phototoxicity, specifically photic retinopathy, also called photic maculopathy. In some embodiments, the photic retinopathy is caused by exposure to the sun. In other embodiments, the photic retinopathy is caused by exposure to the artificial light. The subject can be at risk for photic retinopathy, also known as photic maculopathy. For example, the subject can be undergoing laser procedures to the eye, or can be a welder.

The method can include selecting a subject at risk for retinal degeneration, such as, but not limited to, retinitis pigmentosa, age-related macular degeneration or LCA.

In additional embodiments, subject can have diabetic retinopathy. The methods can included selecting a subject with diabetic retinopathy, or a subject at risk for diabetic retinopathy, such as a diabetic subject.

In some embodiments, the subject has a disease with photoreceptor degeneration features. These include atrophic and exudative age-related macular degeneration, diabetic retinopathy, pathologic myopic degeneration, photic injury to the retina. The disease can arise from a gene mutation, such as retinitis pigmentosa, Stargardt's disease, LCA, or Best's disease. In other embodiments, the subject has a disease in which activated microglia contribute to increased neuroinflammation in the retina. These include, but are not limited to, posterior uveitis, a response to intraocular surgery and retinal laser procedures, a response to viral vectors for gene therapy, and a response to cell-based (e.g., stem-cell) therapy. In further embodiments, the subject has a disease in which neuronal (i.e., non-photoreceptor) degeneration occurs. These include, but are not limited to, glaucoma, retinal artery occlusions, and retinal vein occlusions.

In some examples, the subject has posterior uveitis. Thus subjects can be treated that are affected with toxoplasma retinochroiditis, retinal vasculitis, idiopathic posterior uveitis, ocular histoplasmosis, toxocariasis, cytomegalovirus retinitis, idiopathic retinitis, serpinous choroidopathy, acute multifocal placoid, pigment eptiheliopathy, acute retinal necrosis, bird shot choroidopathy, uveitis associated with a leukemia or a lymphoma, reticulum cell sarcoma, ocular candidiasis, tuberculous uveitis, and lupus retinitis.

Diagnosis can utilize tests which examine the fundus of the eye and/or evaluate the visual field. These include electroretinogram, fluorangiography, and visual examination. The fundus of the eye examination aims to evaluate the condition of the retina and to evaluate for the presence of the characteristic pigment spots on the retinal surface. Examination of the visual field makes possible to evaluate the sensitivity of the various parts of the retina to light stimuli. An electroretinogram (ERG) can be used, which records the electrical activity of the retina in response to particular light stimuli and allows distinct valuations of the functionality of the two different types of photoreceptors (i.e., cone cells and rod cells).

In certain embodiments, the presently disclosed methods can be used to treat any type of retinitis pigmentosa. In some embodiments, the retinitis pigmentosa is caused by mutations in the rhodopsin gene, the peripherin gene, and/or other genes expressed in the rod. The retinitis pigmentosa can be the result of a genetic condition inherited in an autosomal dominant, autosomal recessive or X-linked manner. The X-linked retinitis pigmentosa can be recessive, affecting males, or dominant, so that it affects males and females. The retinitis pigmentosa can be associated with rod-cone retinal degenerations present with central macular pigmentary changes (bull's eye maculopathy). The retinitis pigmentosa can be choroideremia, which is an X-linked recessive retinal degenerative disease. Generally the retinitis pigmentosa (RP) is characterized by the progressive loss of photoreceptor cells.

In additional embodiments, the presently disclosed methods can be used to prevent or treat age-related macular degeneration (AMD). In some embodiments, the subject has atrophic AMD (also called "dry" AMD), wherein the subject has symptomatic central vision loss due to retinal atrophy. In other embodiments, the subject has wet AMD.

In further embodiments, the disclosed methods are of use to treat a subject with LCA.

In some embodiments, the SERM, such as raloxifene, bazedoxifene, arzoxifene, desmethylarzoxifene, tamoxifen and/or a pharmaceutically acceptable salt or derivative thereof, is administered systemically. Systemic modes of administration include oral and parenteral routes. Parenteral routes include, by way of example, intravenous, intrarterial, intramuscular, intradermal, subcutaneous, intranasal and intraperitoneal routes. Components administered systemically may be modified or formulated to target the components to the eye (see above). In a specific non-limiting example, the SERM, such as raloxifene, bazedoxifene, arzoxifene, desmethylarzoxifene, tamoxifen and/or a pharmaceutically acceptable salt or derivative thereof, is administered orally.

The SERM, such as raloxifene, bazedoxifene, arzoxifene, desmethylarzoxifene, tamoxifen and/or a pharmaceutically acceptable salt or derivative thereof, can be administered repeatedly. In some embodiments, the SERM is administered for 10, 15, 20, 25, or 30 days. In further embodiments, SERM is administered for at least 1, 2, 3, 4, 5, 6, 7, 8, 9, 10, 11 or 12 months. In additional embodiments, the SERM can be administered for up to six months, or one year, two years, three years, or longer. In some examples, the SERM can be administered daily, every daily other day, every three days, or weekly for the specified time period. A sustained release formulation, such as a SERM-releasing drug depot or sustained release implant or device, can also be used.

A suitable oral formulation of a SERM, is for example, a tablet or capsule, preferably a tablet containing, for example, about 10, 20, 30 or 40 mg/kg, of therapeutic agent. In some embodiments, the SERM can be administered at a dose in the range of about 20 mg/kg to about 160 mg per day, such as about 20 mg/kg to about 80 mg/kg, for example, about 20 mg/kg to about 40 mg/kg, either as a single dose or as divided doses. In a specific non-limiting example, the dose is administered daily.

In other embodiments, tamoxifen, or a salt or derivative thereof, is administered orally at a dose of about 10 mg/kg to about 80 mg/kg. In other embodiments, tamoxifen, or a salt or derivative thereof, is administered orally at a dose of about 40 mg/kg to about 80 mg/kg. In some examples, tamoxifen, or a salt or derivative thereof is administered orally at a dose of about 40, 45, 50, 55, 60, 65, 70, 75 or 80 mg/kg. In specific non-limiting examples, this dose is administered daily.

In further embodiments, for humans, tamoxifen, or a salt or derivative thereof, is administered orally at a dose of about 0.8 mg/kg to about 6.5 mg/kg daily (≈10 mg/kg/day, approximately equivalent to a 0.81 mg/kg/day dose in an adult human). In some non-limiting examples, the tamoxifen is administered orally at a dose of about 3.2 mg/kg to about 6.5 mg per kg daily. Suitable doses include, but are not limited to, about 0.8 mg/kg, 0.9 mg/kg, 1 mg/kg, 1.1 mg/kg, 1.2 mg/kg, 1.3 mg/kg. 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 4.9 mg/kg, 6.0 mg/kg, 6.1 mg/kg, 6.2 mg/kg, 6.3 mg/kg, 6.4 mg/kg and 6.5 mg/kg. The tamoxifen can be formulated for administration in any oral formulation, including solid or liquid formulations. The tamoxifen can be administered daily.

In some embodiments, tamoxifen, or a salt or derivative thereof, or raloxifene, or a salt or derivative thereof, is administered for 10, 15, 20, 25, or 30 days. In further embodiments, tamoxifen, or a salt or derivative thereof, or raloxifene, or a salt or derivative thereof, is administered for at least 1, 2, 3, 4, 5, 6, 7, 8, 9, 10, 11 or 12 months. In additional embodiments, tamoxifen, or a salt or derivative thereof, or raloxifene, or a salt or derivative thereof, can be administered for up to six months, or one year, two years, three years, or longer. In some examples, tamoxifen, or a salt or derivative thereof, or raloxifene, or a salt or derivative thereof, can be administered daily, every daily other day, every three days, or weekly for the specified time period. In some examples, tamoxifen, or salt or derivative thereof, or raloxifene, or a salt or derivative thereof, is administered daily.

In one non-limiting example, tamoxifen, or a salt or derivative thereof, is administered orally at a dose of about 40 mg/kg to about 80 mg per kg daily for a minimum of 1, 2 3, 4, 5, 6, 7, 8, 9, 10, 11 or 12 months. In other non-limiting examples, tamoxifen, or a salt or derivative thereof, is administered orally at a dose of about 0.8 mg/kg to about 6.5 mg/kg daily for a minimum of 1, 2 3, 4, 5, 6, 7, 8, 9, 10, 11 or 12 months. In additional embodiments, the tamoxifen, or a salt or derivative thereof, can be administered orally for up to six months, or one year, two years, three years, or longer. In some examples, the tamoxifen, or a salt or derivative thereof, can be administered orally, and daily, every daily other day, every three days, or weekly for the specified time period. In some examples, the tamoxifen, or salt or derivative thereof, is administered daily and orally. In some non-limiting examples, tamoxifen, or a salt or derivative thereof, is administered orally at a dose of about 40 mg/kg to about 80 mg per kg daily for at least 3 months, 4, 5, 6, 7, 8, 9, 10, 11 or 12 months. In further non-limiting examples, tamoxifen, or a salt or derivative thereof, is administered orally at a dose of about 0.8 mg/kg to about 6.5 mg/kg daily for at least 3 months, 4, 5, 6, 7, 8, 9, 10, 11 or 12 months.

Dosage treatment may be a single dose schedule or a multiple dose schedule to ultimately deliver the amount specified above. The doses can be intermittent. Moreover, the subject may be administered as many doses as appropriate. In some embodiments, the subject is administered the SERM prior to the onset of a condition.

Without being bound by theory, as the SERM induces a downregulation of inflammatory responses and decreases microglia activation in the retina, and provides protection to photoreceptors and retinal neurons. Pre-treatment administration of the SERM can provide protection to impending or possible events of retinal neuroinflammation and/or photoreceptor injury. These include, and are not limited to: intraocular surgery or ocular procedures involving direct light illumination of the retina, laser or surgical procedures to the retina in which thermal or mechanical damage may be sustained, implantation of retinal devices, intraocular drug-release devices, or intraocular implants, implantation of retinal cells, intraocular delivery of viral vectors, high-risk progression to pathological events in the retina, e.g., impending retinal artery/vein occlusion, vitreous or retinal hemorrhage.

Individual doses are typically not less than an amount required to produce a measurable effect on the subject, and may be determined based on the pharmacokinetics and pharmacology for absorption, distribution, metabolism, and excretion ("ADME") of the subject composition or its by-products, and thus based on the disposition of the composition within the subject. This includes consideration of the route of administration as well as dosage amount, which can be adjusted for local and systemic (for example, oral) applications. Effective amounts of dose and/or dose regimen can readily be determined empirically from preclinical assays, from safety and escalation and dose range trials, individual clinician-patient relationships, as well as in vitro and in vivo assays. Generally, these assays will evaluate retinal degeneration, or expression of a biological component (cytokine, specific inflammatory cell, microglia, etc.) that affects retinal degeneration.

Local modes of administration include, by way of example, intraocular, intraorbital, subconjunctival, sub-Tenon's, subretinal or transscleral routes. In an embodiment, significantly smaller amounts of the components (compared with systemic approaches) may exert an effect when administered locally (for example, intravitreally) compared to when administered systemically (for example, intravenously). In one embodiment, the SERM, such as raloxifene, bazedoxifene, arzoxifene, desmethylarzoxifene, tamoxifen and/or a pharmaceutically acceptable salt or derivative thereof, are delivered subretinally, e.g., by subretinal injection. Subretinal injections may be made directly into the macular, e.g., submacular injection. Exemplary methods include intraocular injection (e.g., retrobulbar, subretinal, submacular, intravitreal and intrachoridal), iontophoresis, eye drops, and intraocular implantation (e.g., intravitreal, sub-Tenons and sub-conjunctival).

In one embodiment, the system disclosed herein is delivered by intravitreal injection. Intravitreal injection has a relatively low risk of retinal detachment. Methods for administration of agents to the eye are known in the medical arts and can be used to administer components described herein.

Administration may be provided as a single administration, a periodic bolus or as continuous infusion. In some embodiments, administration is from an internal reservoir (for example, from an implant disposed at an intra- or extra-ocular location (see, U.S. Pat. Nos. 5,443,505 and 5,766,242)) or from an external reservoir (for example, from an intravenous bag). Components can be administered by continuous release for a particular period from a sustained release drug delivery device immobilized to an inner wall of the eye or via targeted transscleral controlled release into the choroid (see, for example, PCT/US00/00207, PCT/US02/14279, Ambati et al., Invest. Opthalmol. Vis. Sci. 41:1181-1185, 2000, and Ambati et al., Invest. Opthalmol. Vis. Sci. 41:1186-1191, 2000). A variety of devices suitable for administering components locally to the inside of the eye are known in the art. See, for example, U.S. Pat. Nos. 6,251,090, 6,299,895, 6,416,777, 6,413,540, and PCT Publication No. PCT/US00/28187.

In some embodiments, the subject method results in a therapeutic benefit, such as preventing the development of retinal degeneration, halting the progression of a retinal degeneration, and/or reversing the progression of a retinal degeneration. The subject can have any form of retinal degeneration, such as, but not limited to, such as retinitis pigmenosa, age related macular degeneration or LCA.

In some embodiments, the method includes the step of detecting that a therapeutic benefit has been achieved. Measures of therapeutic efficacy will be applicable to the particular disease being modified, and will recognize the appropriate detection methods to use to measure therapeutic efficacy. Suitable tests are disclosed below, and include effects on microglia and ocular motor response. In some non-limiting examples, it is determined whether the SERM reduces retinal microglial activation and pro-inflammatory cytokine expression.

In some embodiments, therapeutic efficacy can be observed by fundus photography or evaluation of the ERG response. The method can include comparing test results after administration of the subject composition to test results before administration of the subject composition.

As another example, therapeutic efficacy in treating a progressive cone dysfunction may be observed as a reduction in the rate of progression of cone dysfunction, as a cessation in the progression of cone dysfunction, or as an improvement in cone function, effects which may be observed by, such as electroretinography (ERG) and/or cERG; color vision tests; functional adaptive optics; and/or visual acuity tests, for example, by comparing test results after administration of the subject composition to test results before administration of the subject composition and detecting a change in cone viability and/or function. In some embodiments, the SERM defers photoreceptor loss, reduces photoreceptor function decrement, and/or reduces visual function loss.

In another example, therapeutic efficacy in treating a vision deficiency can as an alteration in the individual's vision, such as in the perception of red wavelengths, in the perception of green wavelengths, in the perception of blue wavelengths, effects which may be observed by, cERG and color vision tests, for example, by comparing test results after administration of the subject composition to test results before administration of the subject composition and detecting a change in cone and rod viability and/or function. In some embodiments, the method includes evaluation morphology and structure preservation and/or ERG.

The disclosure is illustrated by the following non-limiting Examples.

EXAMPLES

Photoreceptor degeneration is a cause of irreversible vision loss in a number of blinding retinal diseases including retinitis pigmentosa and atrophic age-related macular degeneration for which there is currently no treatment. Two separate murine models of photoreceptor degeneration were used to demonstrate that tamoxifen, a selective estrogen receptor modulator and a drug previously linked with retinal toxicity, exerted potent neuroprotective effects in the retina. In a model of light-induced photoreceptor degeneration, tamoxifen treatment prevented the onset of photoreceptor apoptosis and atrophy and maintained near-normal levels of electroretinographic responses. This rescue was correlated with a reduction of microglial activation and inflammatory cytokine production in the retina in vivo, and a reduction of microglia-mediated toxicity to photoreceptors in vitro, indicating that tamoxifen may confer neuroprotection via the suppression of maladaptive retinal microglial activation. Protective effects of tamoxifen were also observed in the rd10 genetic model for retinitis pigmentosa, conferring significant improvements in retinal structure, electrophysiological responses, and visual behavior. The results demonstrate that, although tamoxifen previously was clinically associated with a low frequency occurrence of retinal changes, it actually exerts broad neuroprotective effects in patients with ongoing photoreceptor degeneration.

Example 1

Materials and Methods

Experimental Animals:

Young adult wild type (WT) C57BL/6J mice and mice homozygous for the Pde6b$^{rd10}$ (rd10) mutation were obtained from The Jackson Laboratory (Bar Harbor, Me.). Postnatal rd10 mice (21-50 days of age) and young adult WT mice (2-3 months of age) of both sexes were raised in cyclic light (~100 lux, 12:12 h) in a National Institutes of Health animal facility. All experiments were conducted according to protocols approved by a local Institutional Animal Care and Use Committee and adhered to the Association for Research in Vision and Ophthalmology (ARVO) Statement animal use in ophthalmic and vision research. For the tamoxifen-treated groups, mice were provided with tamoxifen-supplemented mouse chow (500 mg/kg, Envigo, Indianapolis, Ind.) in place of standard chow for the duration of experiment.

Mouse Model of Retinal Light Injury:

Experimental animals were dark-adapted in a dark room for 7 days and then subjected to pupillary dilation with topical tropicamide (1%, Alcon, Fort Worth, Tex.) and phenylephrine (10%, Alcon, Fort Worth, Tex.). After full dilation, animals were exposed to $2 \times 10^4$ lux of diffuse white fluorescent light (Sunlite Manufacturing, Brooklyn, N.Y.) for 2 hours. After light exposure, mice were maintained in typical conditions of ambient cyclic light (~100 lux, 12:12 h) under which the animals were housed. For tamoxifen-treatment groups, animals were fed a tamoxifen-supplemented chow beginning 7 days prior to light injury, and maintained on the same diet thereafter. Control groups not administered tamoxifen were fed standard mouse chow in separate cages at all time points.

In Vivo Optical Coherence Tomographic (OCT) Imaging and Fundus Autofluorescence Imaging:

Mice were anesthetized with intraperitoneal ketamine (90 mg/kg) and xylazine (8 mg/kg) and their pupils were dilated. Retinal structure was assessed using an optical coherence tomographic (OCT) imaging system (Bioptigen, Durham, N.C.). To document retinal changes in the light injury model, animals were imaged prior to dark adaptation and subsequently at different times following light exposure. Volume scans of 1.4 mm by 1.4 mm centered on the optic nerve (1000 A-scans/horizontal B-scan, 33 horizontal B-scans, average of three frames per B-scan, each spaced 0.0424 mm apart) were captured. Retinal thickness measurements in each quadrant of a circular grid of diameter 1.2 mm were computed using the manufacturer's software. Total retinal thickness (measured from the vitreal surface to the RPE layer) and outer retinal thickness (measured from the vitreal surface of the outer plexiform layer to the vitreal surface of the RPE layer) were recorded from OCT images following automated retinal segmentation. To document retinal changes in rd10 mice, additional horizontal and vertical linear scans (1.4 mm width, 1000 A-scans/B-scan, average of 20 frames/B-scan) were obtained with the scan centered on the optic nerve head. In these vertical and horizontal B-scans, the area of ONL in the scan was circumscribed and measured manually. Average outer retinal thickness was computed by dividing the outer retinal area with the length of measured retina. Fundus autofluorescence imaging was performed using a confocal scanning laser ophthalmoscopy (cSLO, Heidelberg Engineering, Heidelberg, Germany) with 488 nm wavelength excitation. Fundus images were obtained over the central 30° angle with the field centered on the optic nerve head.

Electroretinographic Analysis:

Electroretinographs (ERGs) were recorded using an Espion E$^2$ system (Diagnosys, Littleton, Mass.). Mice were anesthetized as described above after dark adaptation overnight. Pupils were dilated and a drop of proparacaine hydrochloride (0.5%, Alcon) was applied on cornea for topical anesthesia. Flash ERG recordings were obtained simultaneously from both eyes with gold wire loop electrodes, with the reference electrode placed in the mouth and the ground subdermal electrode at the tail. ERG responses were obtained at increasing light intensities over the ranges of $1 \times 10^{-4}$ to 10 cd·s/m$^2$ under dark-adapted conditions, and 0.3 to 100 cd·s/m$^2$ under a background light that saturates rod function. The stimulus interval between flashes varied from 5 s at the lowest stimulus strengths to 60 s at the highest ones. Two to 10 responses were averaged depending on flash intensity. ERG signals were sampled at 1 kHz and recorded with 0.3 Hz low-frequency and 300 Hz high-frequency cutoffs. Analysis of a-wave and b-wave amplitudes was performed using customized Espion ERG Data Analyzer software (v2.2) that digitally filters out high frequency oscillatory potential wavelets. The a-wave amplitude was measured from the baseline to the negative peak and the b-wave was measured from the a-wave trough to the maximum positive peak. For light injury model, ERGs were recorded at 1 week after light exposure. For rd10 mice, ERGs were recorded at P29 and P50. Statistical significance between non-treated control and tamoxifen-treated mice was analyzed using a 2-way ANOVA.

Measurement of Optokinetic Response (OKR):

Optokinetic responses (OKR) of awake, behaving mice to visual stimuli in the form of a moving grating were measured using a custom-designed apparatus (Kretschmer et al., Journal of Neuroscience Methods, 2015). Optokinetic responses were measured in rd10 mice with tamoxifen treatment (treatment started at P21) and non-treated control at P49 (n=7 animals in control group, n=9 animals in tamoxifen-treated group) as previously described (Wang et al., 2016). Briefly, mice were positioned on a platform and presented with sinusoidal gratings at maximum contrast at spatial frequencies of 0.025, 0.05, 0.1, 015, 0.2, 0.25, 0.3, 0.35, 0.4, 0.425, and 0.45 cycles/degree at a stimulus speed of 12 deg/s on four LCD screens that surround the tested animal. Stimuli presentation was controlled using an open source software program to produce a virtual cylinder that maintains a constant distance between the grating and horizontal visual field of the tested animal located at the center of the apparatus.

To measure elicited optokinetic motor reflexes (OMR), the head movements of the unrestrained tested animal were video-recorded by a camera placed above the animal and analyzed by an algorithm that tracks the position of the mouse's head. This data is used to automatically readjust the presentation of the stimuli to changing head positions to keep the size of the gratings constant (the analysis software used, OmrArena, was modified from a version previously published)(Kretschmer et al., 2013). OMR measurements were objectively obtained using an automated approach during off-line analysis and do not involve subjective grading or input from a human observer. OMR tracking behavior was quantified as the ratio of the total amount of time the animal's head moved in the stimulus direction and the amount of time where the head moved against the stimulus direction ($T_{correct}/T_{incorrect}$). Each animal was measured under each condition five times for one minute. OMR was recorded under photopic ($9\times10^{10}$ Q·s/cm$^2$) light conditions. Estimations of visual threshold, defined as the spatial frequency corresponding to 25% of the maximum optomotor response, were also calculated. Statistical significance between non-treated control and tamoxifen-treated mice was analyzed using unpaired t-test.

Immunohistochemistry and TUNEL Labeling of Retinal Tissue:

Mice were euthanized by $CO_2$ inhalation and their eyes removed. Enucleated eyes were dissected to form posterior segment eye-cups which were then fixed in 4% paraformaldehyde (PFA) in phosphate buffered saline (PBS) for 2-4 hours at 4° C. Eyecups were either processed for vibratome sectioning (100 µm thick sections, VT1000, Leica) or dissected to form retinal flat-mounts. Flat-mounted retinas or retinal sections were blocked overnight in blocking buffer containing 6% normal donkey serum (NDS) and 0.5% Triton X-100 in PBS at room temperature. Primary antibodies (Iba1, 1:500, Wako, Richmond, Va.; CD68, 1:500, Bio-Rad, Raleigh, N.C.) were diluted in blocking buffer and applied overnight for sections and flat-mounts at 4° C. on a shaker. After washing in 1×PBS with 0.5% Triton X-100, sections were incubated overnight with secondary antibodies (Alexa Fluor-488 (or 568)-conjugated donkey anti-rabbit or rat IgG respectively, and DAPI (1:500; Sigma) to label cell nuclei. Apoptosis of retinal cells was assayed using a terminal deoxynucleotidyl transferase dUTP Nick End Labeling (TUNEL) assay (Roche, Indianapolis, Ind.) according to the manufacturer's specifications. Stained retinal sections were imaged with confocal microscopy (FluoView 1000, Olympus). Multiplane z-series were collected using a 20× objective; each z-series spanned 20 µm in depth, with each section spaced 1 µm apart. Confocal image stacks were viewed and analyzed with FV100 Viewer Software (Olympus) and Image J (NIH). Mean thickness measurements of the ONL and cell densities (TUNEL$^+$, Iba1$^+$ and CD68$^+$ cells) were computed over 20× imaging fields obtained in the mid-peripheral retina in the superotemporal quadrants.

Cell Culture and Cell Viability Assay:

Retinal microglia were isolated from 1-2 month old C57BL/6J wild type mice as previously described (Ma et al., Neurobiology of aging 34:943-960, 2013). Briefly, retinal cells were dissociated by digestion in 2% papain, followed by trituration and centrifugation. Resuspended cells were transferred into 75-cm$^2$ flasks containing Dulbecco's Modified Eagle Medium (DMEM): NutrientMixture F-12 media with 10% fetal bovine serum (FBS) (Gibco, Carlsbad, Calif., USA) and nonessential amino acids solution (Sigma, St. Louis, Mo., USA). Following overnight culture, the medium and any floating cells were discarded and replaced with fresh medium. When the cells grow to confluence, culture flasks were shaken gently to detach microglial cells, which were subcultured in 6-well plates. Subcultured microglia ($2.5\times10^5$ cells/well in a 6-well plate) were exposed to tamoxifen (0, 1, 5, and 10 µg/ml) for 2 hours, followed by 1 µg/ml LPS for 16 hours, and then assessed for protein expression of inflammatory cytokines.

Murine microglial cell line (BV-2) cells and photoreceptor-like cell line (661W) were used in this study. BV-2 cells were plated in 6-well plates at the density of $4\times10^5$/well and cultured for 24 h in DMEM medium (Life Technologies Corporation, Grand Island, N.Y.) containing 5% heat inactivated FBS (Life Technologies Corporation, Grand Island, N.Y.) at 37° C. in a humidified atmosphere of 5% CO2. BV-2 cells were preincubated for 24 h with tamoxifen (1, 5 or 10 µg/ml, Sigma-Aldrich, St Louis, Mo.) or 0.5% ethanol as vehicle control. After preincubation with the proteasome inhibitor ALLN (100 µg/ml, Santa Cruz Biotechnology, Dallas, Tex.) for 30 min, BV-2 cells were stimulated with 50 ng/ml lipopolysaccharide (LPS, Sigma-Aldrich, St Louis, Mo.) for 6 h before conditioned media were collected. To investigate the ability of tamoxifen to decrease microglia-mediated neurotoxicity, 661W cells were placed in 96-well plate at $4\times10^4$/well for 6 h and then incubated for 48 h with culture supernatants from control, 5 µg/ml Tamoxifen−, 50 ng/ml LPS−, 1 µg/ml Tamoxifen+50 ng/ml LPS−, 5 µg/ml Tamoxifen+50 ng/ml LPS−, or 10 µg/ml Tamoxifen+50 ng/ml LPS-treated BV-2 microglia. Cell viability of 661W photoreceptors were assessed using a MTT cell proliferation assay kits (ATCC, Manassas, Va.) following the manufacturer's specifications.

Measurement of Cytokine Levels:

Cultured cells or retinas were lysed by trituration in protein lysate buffer (Complete Ultra, Roche) with proteinase inhibitor cocktail (Calbiochem, Gibbstown, N.J.) at 4° C. Following sonication and centrifugation, protein concentration was measured (BCAprotein assay kit, Pierce). Cytokine levels were determined using a MilliplexVR assay kit (Milliplex MAP mouse cytokine/chemokine magnetic bead panel, #MCYTOMAG-70K, Millipore Corp) using the Luminex MAPIX system with data analysis using xPONENT 4.2 software (Luminex Corporation).

Statistical Analysis:

Statistical analyses were performed using statistical software (Graphpad, San Diego, Calif., USA). For comparisons involving two data columns, t-tests (paired or unpaired) or non-parametric tests (Mann-Whitney) were used, depending on whether the data followed a Gaussian distribution as determined by normality tests. For comparison involving 3 or more data columns, a one-way ANOVA (with Dunnett's multiple comparison test) was used if the data followed a Gaussian distribution and a non-parametric Kruskal-Wallis test (with Dunn's multiple comparison test) was used if it did not. Data sets from tamoxifen-treated vs control diet-treated animals were compared using a 2-way ANOVA. The Chi-square statistic was used to compare the prevalence of retinal detachments in tamoxifen-treated vs control diet-treated animals. A P value <0.05 was set as the basis for rejecting the null hypothesis. Error bars in graphs indicate standard error (SE).

Example 2

Figure 5A:
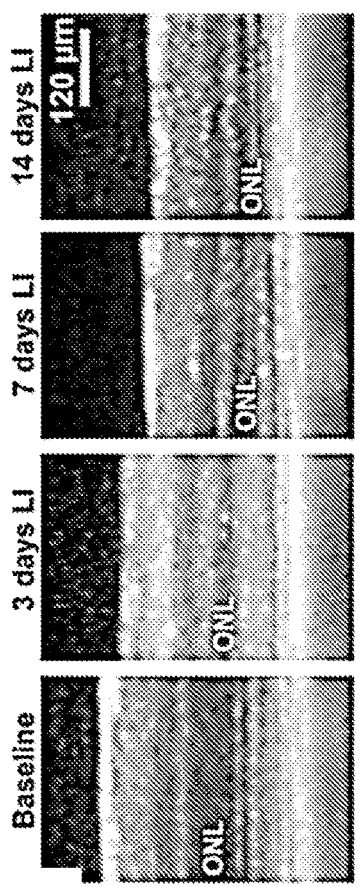
Figure 5B:
Figure 5C:
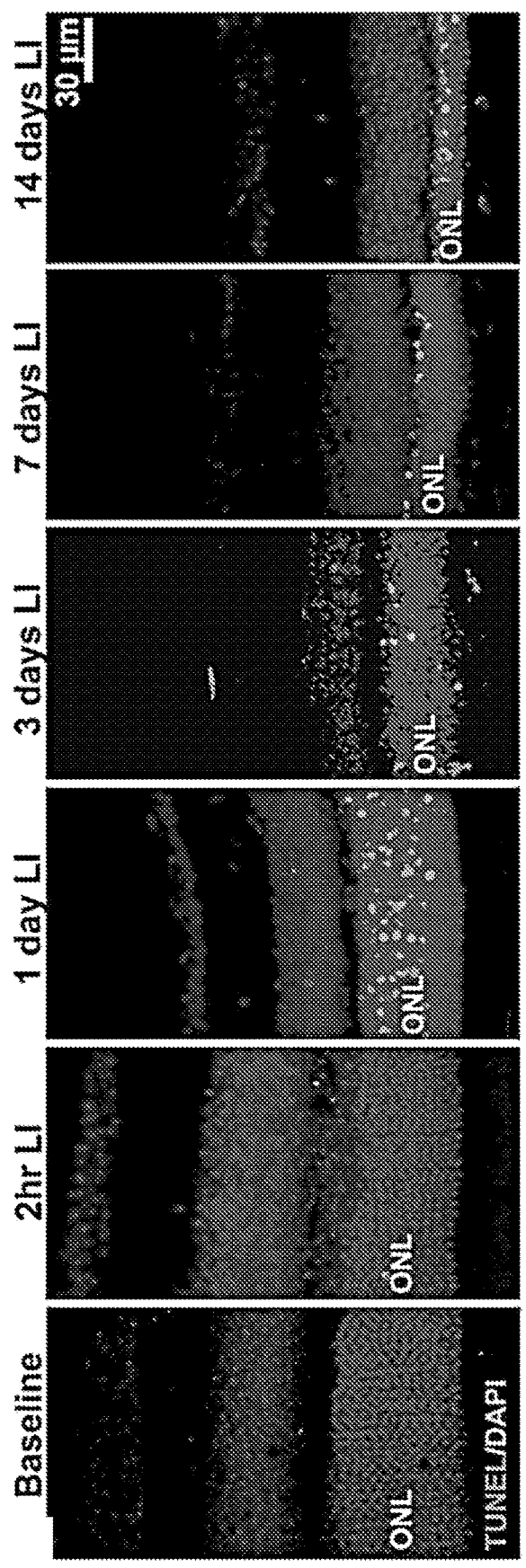

Model of Light-Induced Injury Results in Photoreceptor Apoptosis and Loss of Photoreceptor Function Wild type adult (2-3 month old) C57B16/J mice were subjected to light injury (LI) and the effects of LI analyzed using in vivo OCT imaging and histology. OCT imaging in the central retina revealed widespread overall retinal thinning 7 days post-LI that was most prominent in the superotemporal quadrant of the retina (FIG. 5A). OCT B-scans obtained in the superotemporal quadrant demonstrated a progressive thinning of the outer nuclear layer (ONL) over the first 7 days post-LI that subsequently stabilized (FIG. 5B). Histological analysis in retinal sections obtained in equivalent retinal positions showed the prominent emergence of TUNEL-positive photoreceptors at 1 day and 3 days post-LI which decreased after 7 days (FIG. 5C, D). Quantification of ONL thicknesses in histological analyses of retinal sections corroborated the temporal pattern of retinal thinning observed on in vivo OCT imaging (FIG. 5E). LI also induced significant decrements in dark- and light-adapted ERG a- and b-wave amplitudes 7 days post-LI (FIG. 5F, G), indicating concurrent loss of rod and cone photoreceptor function. Together, this current model of light-induced injury in adult C57Bl6/J mice effectively induces an acute and time-limited injury specifically to photoreceptors that is evident structurally as apoptotic photoreceptor loss and functionally as decreased responses to light stimuli.

Example 3

Figure 1A:
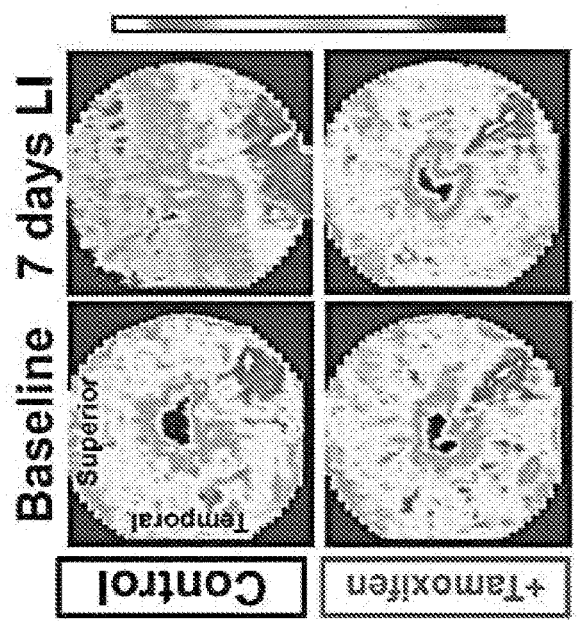
Figure 6:
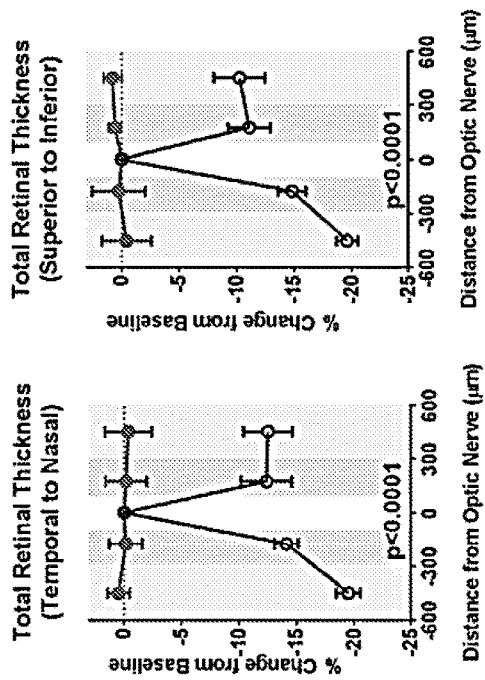
FIG. 6. Tamoxifen-mediated rescue of photoreceptor degeneration in light injury model is not dependent on the sex of experimental animals. Young adult (2-3 month old) female and male mice were subjected to light injury (LI) with and without pretreatment with tamoxifen. OCT evaluation of total retinal thickness (top panels) and outer retinal thickness (bottom panels) demonstrated that significant protection was conferred in both male and female animals treated with tamoxifen relative to sex-matched untreated controls (p values from 2-way ANOVA, n=17 treated and 17 untreated control female animals, 10 treated and untreated 10 control male animals).
Figure 6:
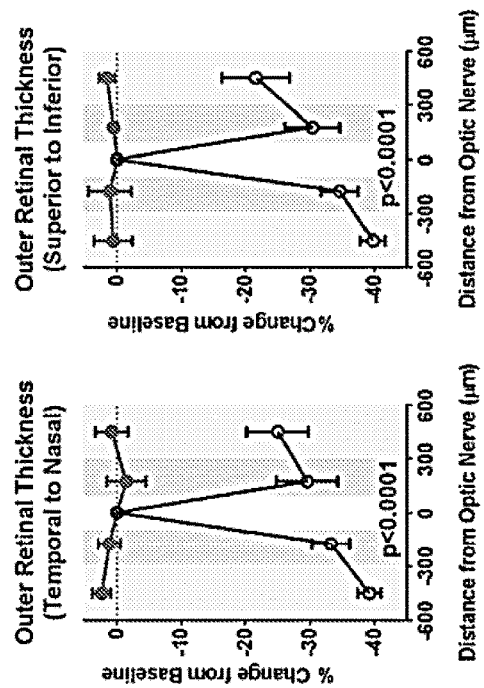
Figure 6:
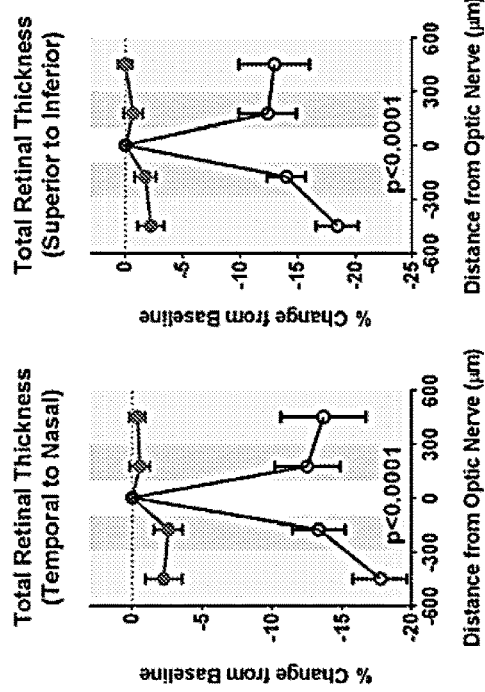
Figure 6:
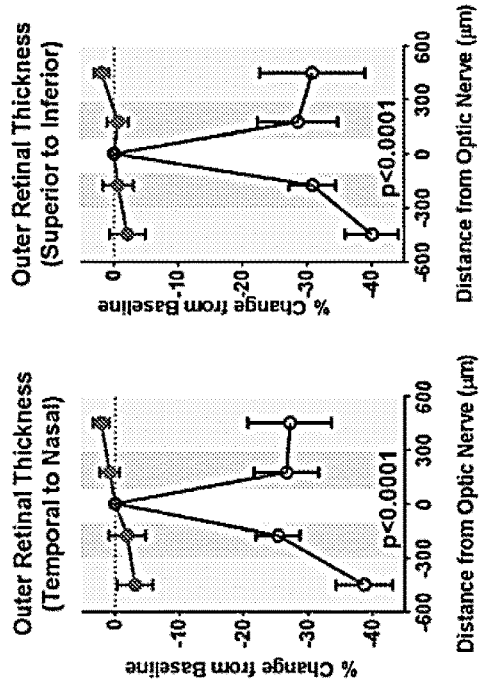
Figure 7A:
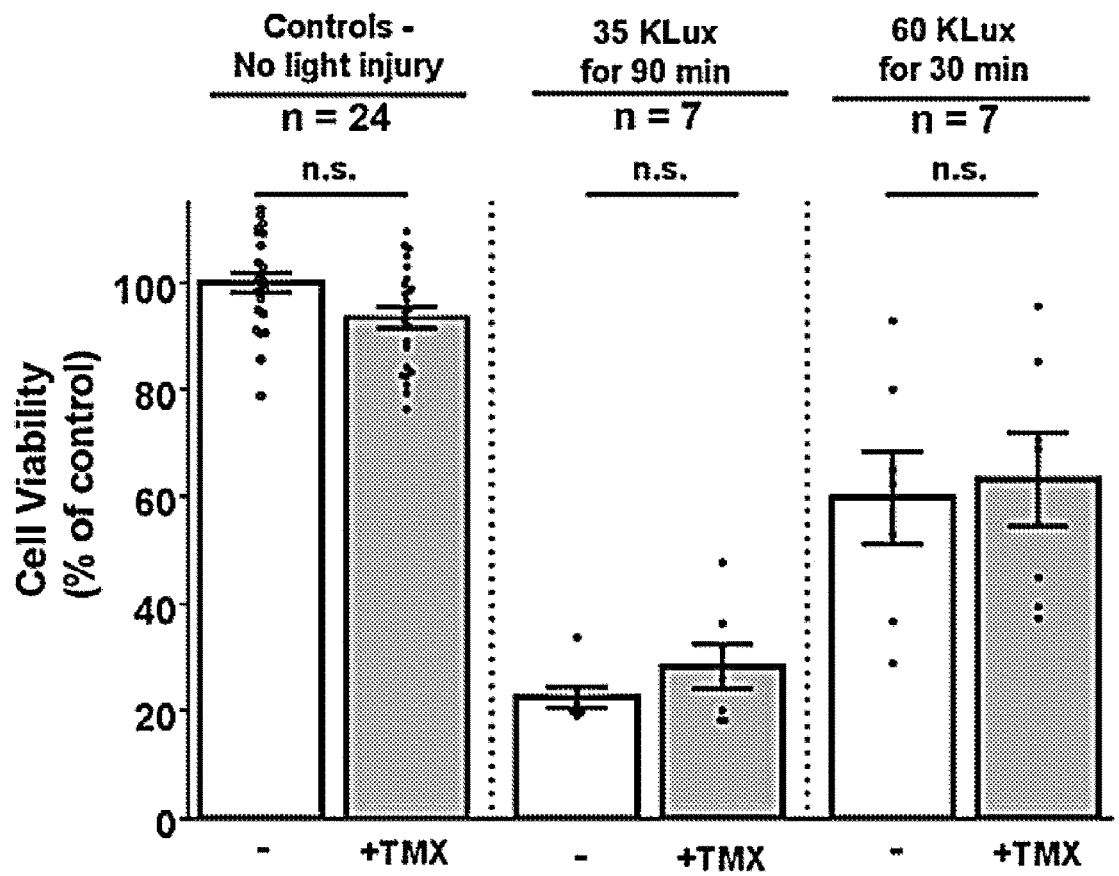
FIGS. 7A-7B. Evaluation of the effects of tamoxifen on photoreceptor survival and function. (A) The direct effect of tamoxifen on photoreceptor survival was evaluated in vitro using a light-induced injury model. 661W photoreceptors cultured in a 96-well plate ($4\times10^4$ cells/well) were subjected to two regimens of photic injury; the conditions were (1) control conditions (no light injury), (2) under $35\times10^3$ lux for 90 min (severe injury), and (3) under $60\times10^3$ lux for 30 min (moderate injury). Cultured photoreceptors were either cultured under standard conditions or pre-treated with tamoxifen (5 µg/ml for 24 hours) before light injury. Cell survival was measured 12 h following injury using a MTT assay. Tamoxifen pre-treatment did not result in any significant changes in photoreceptor survival relative to controls under all conditions (n=indicates independent replicates, n.s. indicates p>0.05, 1-way ANOVA, Sidak's multiple comparisons test). (B) Measurement of ERG recovery following a moderate bleaching flash in animals pre-treated for oral tamoxifen for 7 days compared to age-matched control fed a standard control diet. The amplitudes of the a-wave of ERGs following bleach were recorded every 2 min at a flash intensity of 10 cd·s/m² for the two groups of animals, and mean a-wave recovery with time were plotted. Mean a-wave amplitudes recovered to baseline conditions at similar times and the dynamics of recovery were not significantly different between the two groups (2-way ANOVA, p=0.493), indicating that tamoxifen-pretreatment did not affect photoreceptor dark-adaptation function.
Figure 7B:
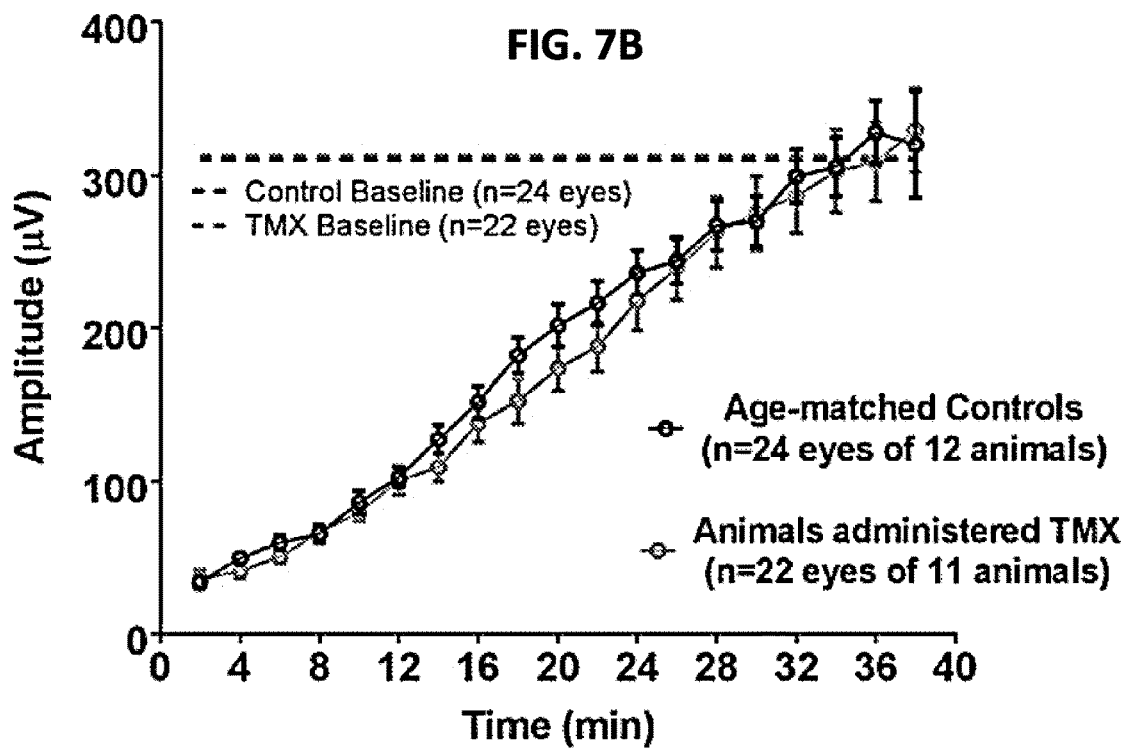

Tamoxifen Administration Provides Complete Structural and Functional Photoreceptor Rescue in the Model of Light Injury Experimental animals were administered tamoxifen as a supplement in standard mouse chow (estimated 80 mg/kg intake of tamoxifen per day) beginning 1 week prior to LI, and continued following LI. Age-matched control animals were provided with standard chow (without added tamoxifen) and housed in separate cages alongside tamoxifen-treated animals in similar lighting environments. At 7 days post-LI, the typical thinning of the retina centered in the superotemporal quadrant that was observed in control animals on OCT imaging was absent in all tamoxifen-treated animals (FIG. 1A). Similarly, the thinning of the ONL layer and the presence of shallow retinal detachments observed on individual OCT B-scans in control animals were also generally absent in tamoxifen-treated animals (FIG. 1B). Quantification of total retinal thicknesses and outer retinal thicknesses from OCT images following automated segmentation in 8 separate retinal positions (100-300 µm and 300-600 µm in each of the superior, inferior, temporal, and nasal quadrants around the optic nerve) demonstrated retinal thicknesses in all retinal positions to be significantly greater at 7 days in tamoxifen-treated animals relative to controls (FIG. 1C). In tamoxifen-treated animals, the laminated appearance of the retina and retinal thicknesses at 7 days post-LI were nearly identical to those obtained at baseline. The above results were obtained by pooling data from animals from both sexes; when the data was separately analyzed for female (n=17 control, 17 tamoxifen-treated) and male (n=10 control, 10 tamoxifen-treated) animals, we noted similar protective effects on retinal structure in animals of both sexes (FIG. 6). Taken together, tamoxifen administration provided near-complete structural rescue in the model of light-induced photoreceptor injury in a manner that was independent of the sex of the animal.

The prevalence of shallow separation of the neural retina from the RPE (i.e. retinal detachments) was assessed in the experimental groups using OCT. Retinal detachment is a feature of outer retina degeneration that is also observed in mouse models of inherited photoreceptor degeneration (Pennesi et al., Invest Ophthalmol Vis Sci 53:4644-4656, 2012). The prevalence of retinal detachments in 3 separate experimental repeats were all significantly lower in tamoxifen-treated vs. control animals (FIG. 1D), with the overall prevalence being 1/27 vs. 13/27 in tamoxifen-treated vs. control animals respectively (Chi-square statistic=13.9, p=0.0002).

Figure 1E:
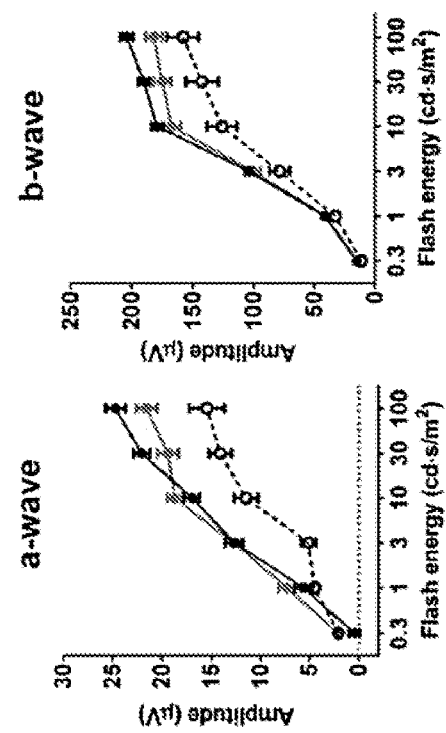
Figure 1E:
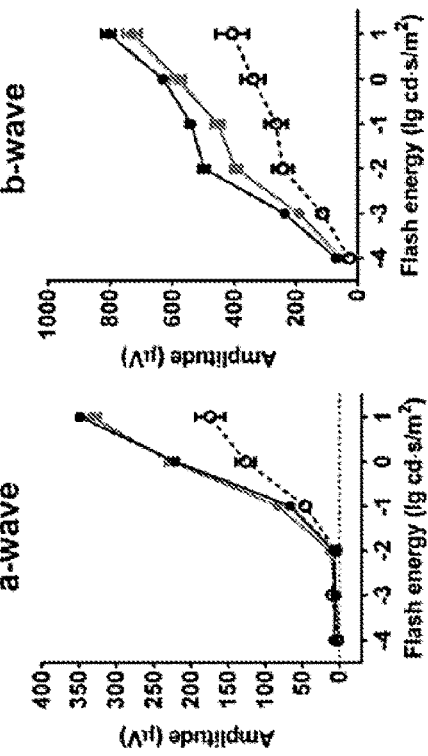
Figure 1E:
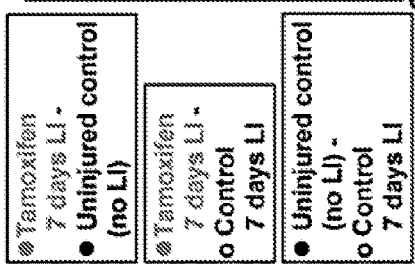

ERG evaluations were performed on tamoxifen-treated and control animals 7 days post-LI, as well as on uninjured, age-matched controls. Following LI, tamoxifen-treated animals demonstrated significantly greater a- and b-wave amplitudes for both dark- and light-adapted ERGs relative to control animals (FIG. 1E). The ERG amplitudes in tamoxifen-treated animals post-LI approached those in age-matched uninjured controls, indicating that a near-complete functional rescue effect was induced by tamoxifen-treatment, correlating to the marked structural protection observed on OCT.

Example 4

Figure 2B:
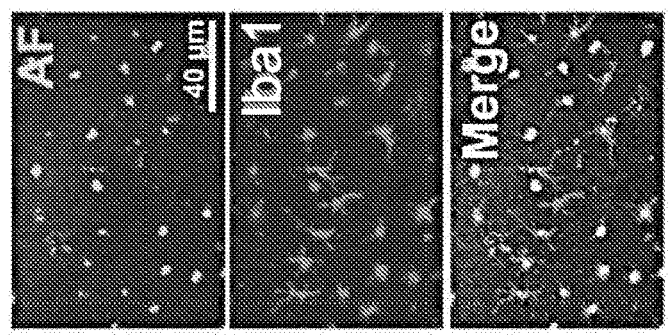
Figure 2A:
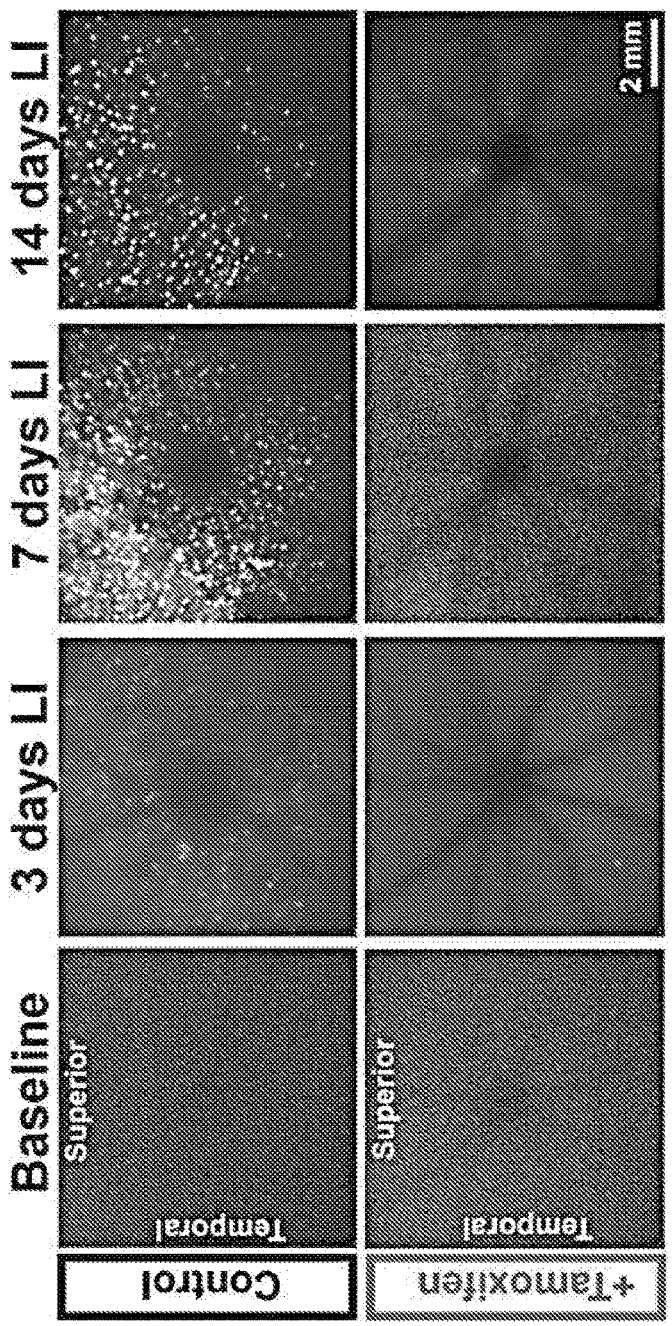

Tamoxifen Treatment Reduces Microglial Infiltration and Activation Induced by Light Injury In vivo fundus autofluorescence imaging was performed in tamoxifen-treated and control animals before and at different times following LI. Prior to LI, minimal autofluorescence was observed on fundus imaging. In animals fed a control diet, imaging performed 3 days post-LI demonstrated the appearance of isolated autofluorescent spots near the optic nerve. These spots subsequently increased in number and intensity particularly in the superotemporal quadrant at 7 days post-LI, before decreasing in intensity and number at 14 days post-LI (FIG. 2A). In tamoxifen-treated animals, minimal to no fundus autofluorescent signals were observed at all time points monitored. To discover the basis for these autofluorescent spots, flat-mounted retina tissue was prepared from control animals at 14 days post-LI. On confocal imaging, autofluorescent spots matching the size and distribution of those observed on in vivo fundus autofluorescence imaging were observed at the level of the outer retina (FIG. 2B). These autofluorescent spots colocalized well with Iba1 immunopositivity, indicating them to arise from autofluorescent retinal microglia that have infiltrated into the outer retina following LI, as observed in other models of subretinal microglia accumulation (Ma et al., Neurobiology of aging 34:943-960, 2013).

To characterize the distribution and activation of retinal microglia following LI, and the effect of tamoxifen administration on these features, retinal microglia were examined in retinal sections at different times after LI using Iba1 immunohistochemistry. In control animals, beginning as early as 1 day post-LI, microglia in the inner retina were observed to extend their processes into the ONL and begin infiltrating the photoreceptor layer concurrently with the emergence of TUNEL-positivity in the ONL (FIG. 2C). Microglia infiltration in control animals continued to persist in the ONL (FIG. 2G) and in the subretinal space (FIG. 3H), up to 14 days post-LI. The number of activated CD68-immunopositive microglia also increased in the subretinal space beginning at 3 days post LI (FIG. 2D, I). These observations indicate that the infiltration of activated microglia into the photoreceptor layer occurred early in LI-induced degeneration and was present concurrently during the period of photoreceptor apoptosis and degeneration. In the tamoxifen-treated group, minimal decreases in ONL thickness were observed following LI, corroborating observations on OCT (FIG. 2E). Minimal TUNEL-labeling was also observed (FIG. 2F). The morphology, distribution, and activation status (as revealed by CD68 labelling) were also minimally changed from uninjured controls at all timepoints following LI (FIG. 2G-I). This data demonstrate that while microglial activation and infiltration were early and prominent features in the LI model, these microglial changes were largely inhibited with tamoxifen treatment.

Example 5

Figure 3A:
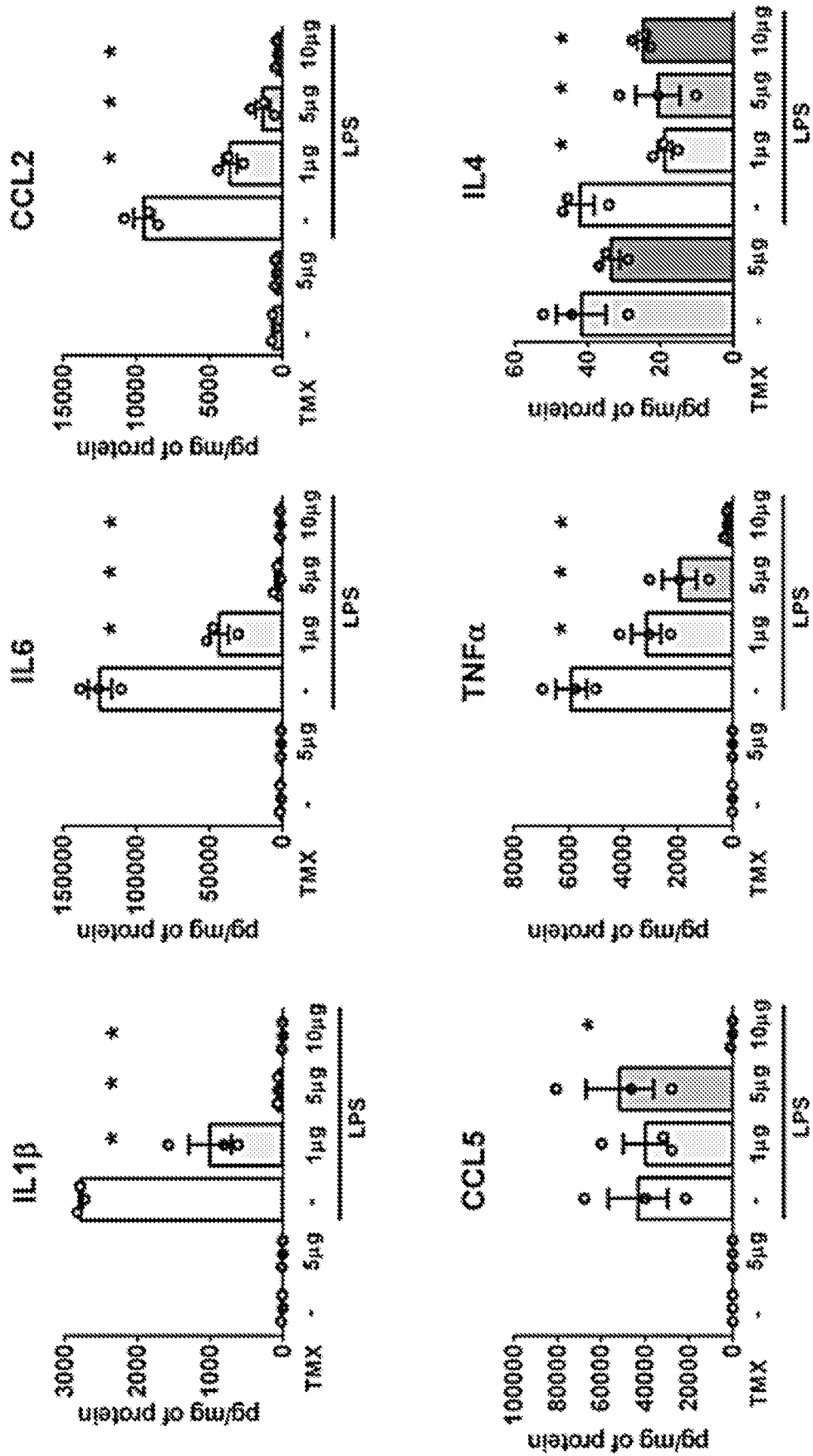
FIGS. 3A-3C. Tamoxifen administration suppresses microglial activation and inflammatory cytokine production and reduces microglial toxicity to photoreceptors. (A) The effect of tamoxifen (TMX) on retinal microglia activation and inflammatory cytokine expression was assessed in vitro. Microglia cultured from the retina of young adult mice (1-2 months of age, $2.5 \times 10^5$ cells/well in a 6-well plate) were exposed to tamoxifen (0, 1, 5, and 10 μg/ml) for 2 hours, followed by 1 μg/ml LPS for 16 hours, and then assessed for protein expression of inflammatory cytokines. In the absence of LPS, protein levels of inflammatory cytokines in microglia cell lysates were at low basal levels and were unchanged with exposure to tamoxifen (5 μg) alone. LPS-induced expression of cytokines in microglia was significantly reduced by tamoxifen pre-treatment in a dose-dependent manner (n=3 repeats per condition, * indicates p<0.05 for comparisons relative to the LPS only group, 1-way ANOVA). (B) The ability of tamoxifen treatment to influence inflammatory cytokine production in the retina in vivo was evaluated in the acute light injury (LI) model. Inflammatory cytokines levels were assessed in retinal tissue from 2-3 month old control animals (not subject to light injury), light-injured controls not treated with tamoxifen (3 days post-LI), and tamoxifen-treated animals (3 days post-LI). While comparisons did not reach statistical significance, multiple cytokines demonstrated increases following LI in the absence of tamoxifen, that were reduced to close to baseline levels with tamoxifen treatment (n=3-6 animals in 2 separate trials). (C) The ability of tamoxifen to decrease microglia-mediated neurotoxicity was evaluated in a microglia-photoreceptor interaction model. 661W photoreceptors cultured in 96-well plate ($4 \times 10^4$ cells/well) were exposed to conditioned media from LPS-stimulated (50 ng/ml) BV2 microglia (cultured in 6-well plate with a cell density of $4 \times 10^5$ cells/well) for 48 h. Prior to LPS-stimulation, BV2 microglia were pre-treated with varying doses of tamoxifen (1, 5 or 10 μg/ml). Cell viability of 661W photoreceptors were assessed using a MTT assay. Pre-treatment with tamoxifen (5 and 10 μg/ml) significantly reduced neurotoxicity of microglia-conditioned media (* indicates P<0.0001, 1-way ANOVA, comparison with LPS-only control, n=16 independent replicates). Exposure of 661W photoreceptors to vehicle (0.5% ethanol) or tamoxifen (5 μg/ml) alone had no effect on viability.
Figure 3B:
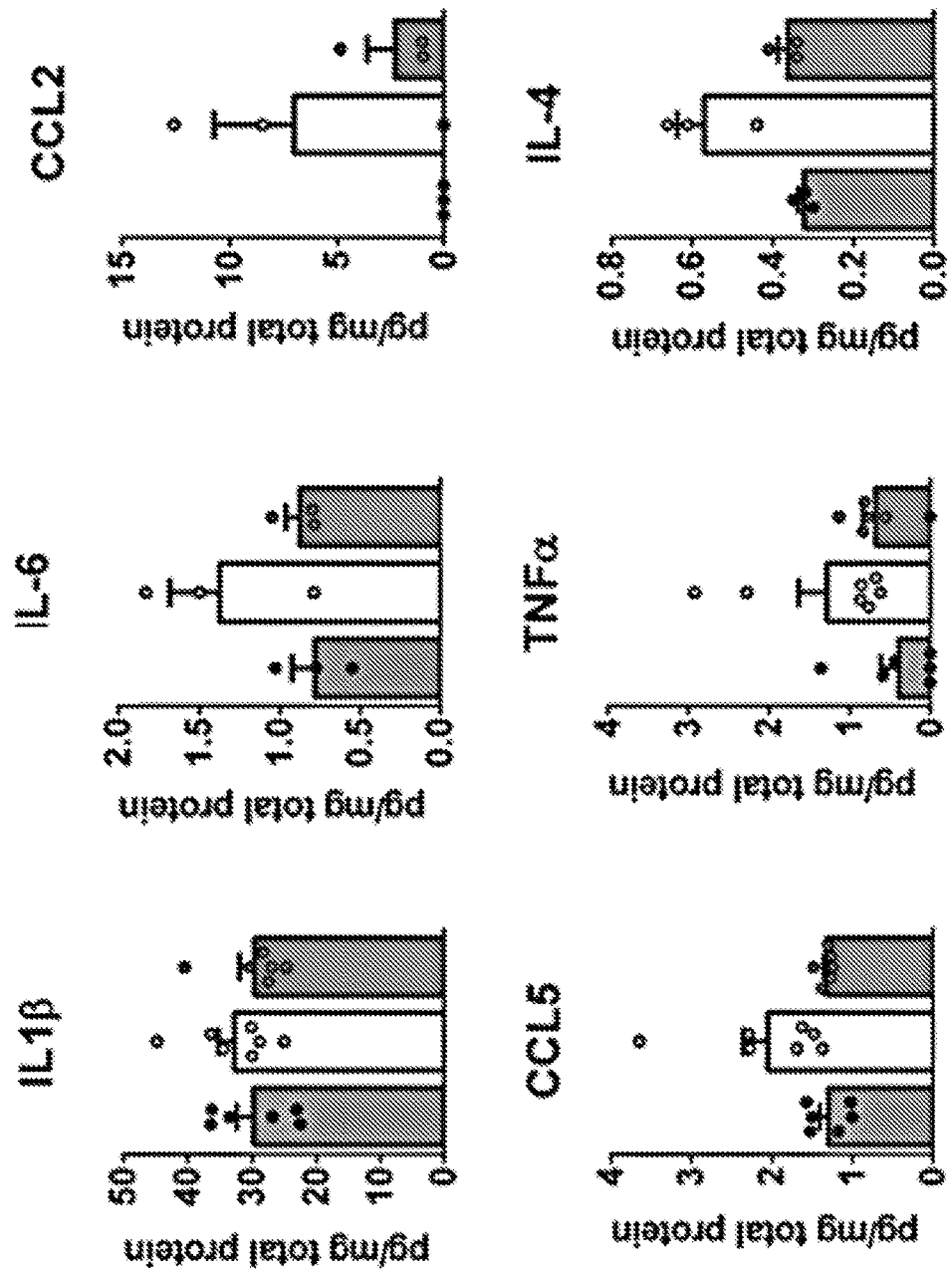

Tamoxifen Administration Suppresses Microglial Activation and Inflammatory Cytokine Production and Reduces Microglial Toxicity to Photoreceptors To directly assess the effect of tamoxifen on microglia, cultured retinal microglia were exposed to tamoxifen and the effect of tamoxifen pre-treatment on lipopolysaccharide (LPS)-induced microglial upregulation of key inflammatory cytokines was evaluated. It was found that tamoxifen administration alone, in the absence of LPS stimulation, had minimal effect on cytokine expression (FIG. 3A). However, tamoxifen pre-treatment of microglia significantly inhibited the upregulation of cytokine expression in response to LPS. These tamoxifen effects were dose-dependent, with greater doses inducing greater inhibition to LPS stimulation in the 1-10 μg range, indicating that tamoxifen can act directly on microglial cells to reduce their pro-inflammatory responses to injury-related stimuli. It was also assessed whether tamoxifen treatment prior to LI also decreased proinflammatory cytokine production in the retina in vivo. Protein assessment of cytokine levels in whole retina from tamoxifen-treated animals relative to control diet-treated animals, while not decreased to a statistically significant extent, demonstrated a general trend of decrease towards baseline levels in the non-injured retina (FIG. 3B), indicating that tamoxifen pre-treatment could inhibit microglial upregulation of cytokines in responses to LI in vivo.

Figure 3C:
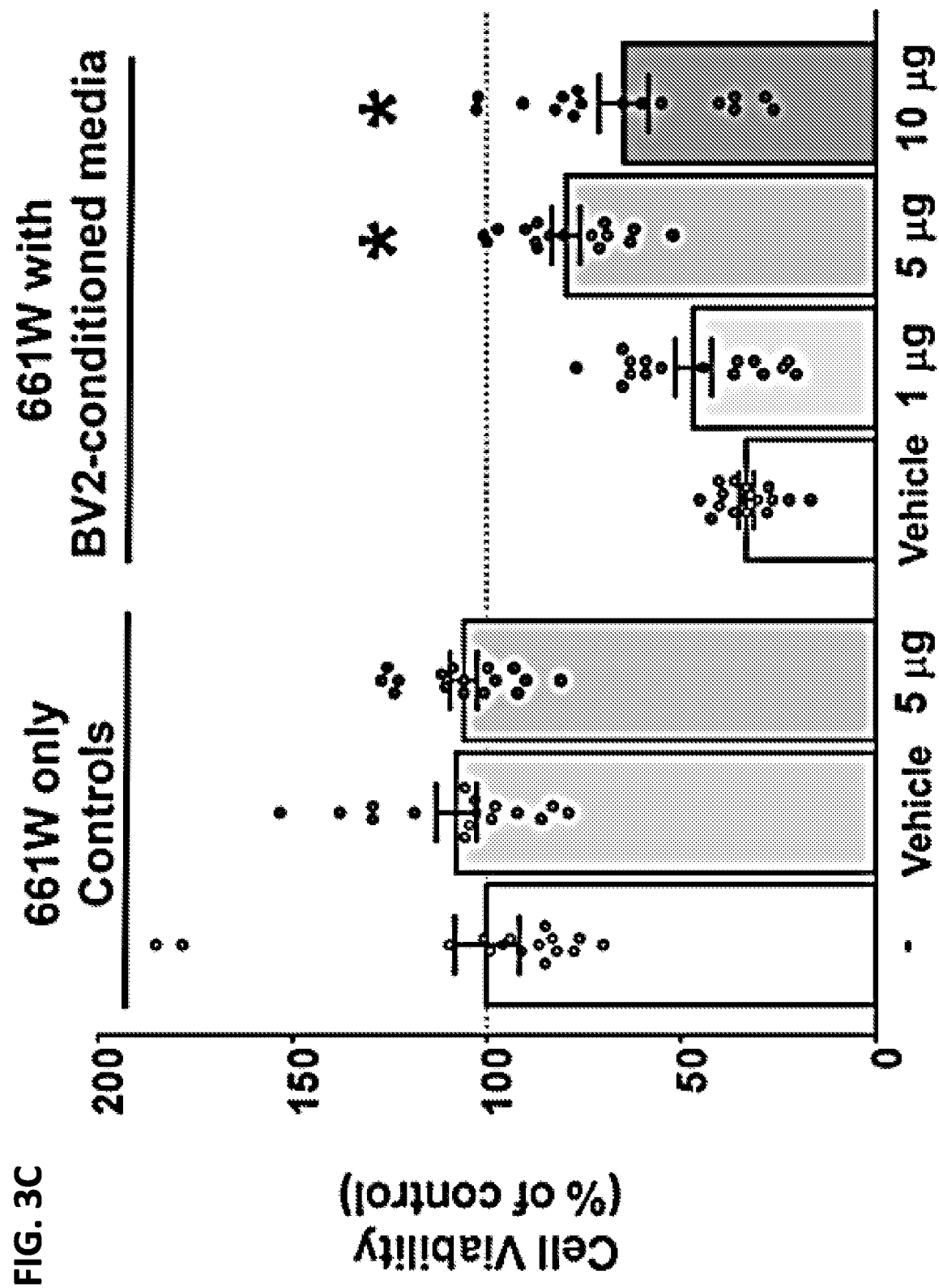

To relate the inhibition of microglial activation to photoreceptor degeneration, an in vitro microglia-photoreceptor interaction assay was performed in which 661W cells from a photoreceptor cell line were exposed to conditioned media from LPS-stimulated BV2 microglia. While control media from LPS-stimulated microglia can induce decreased photoreceptor viability, this negative effect was reduced by the pre-treatment of BV2 cells with tamoxifen (FIG. 3C), with larger doses (5-10 μg) providing greater rescue of 661W viability. Tamoxifen (5 μg) on its own did not exert any effect on the viability of 661W photoreceptors. These results together indicate that tamoxifen treatment can limit the activation of microglia to injury signals and thus reduce the consequent proinflammatory neurotoxic effects on photoreceptors.

Example 6

Figure 4A:
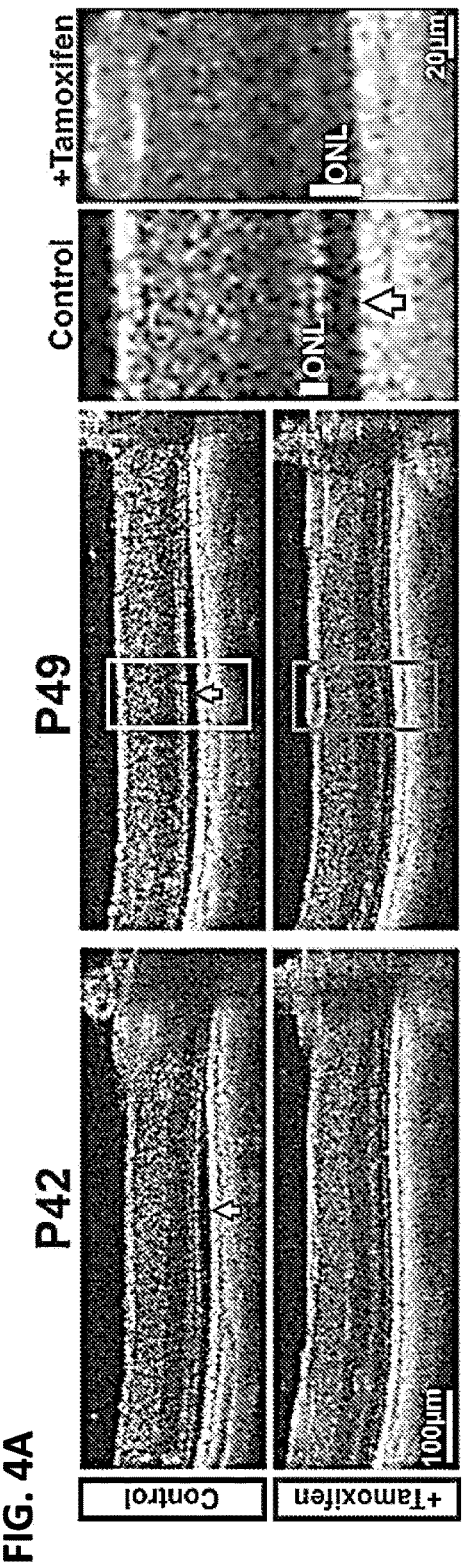
FIGS. 4A-4D. Tamoxifen administration provides structural and functional rescue of photoreceptor degeneration in rd10 mouse model for retinitis pigmentosa. rd10 mice were provided either standard chow (control group) or tamoxifen-supplemented chow from P21 and evaluated at different time points during photoreceptor degeneration. (A) In vivo OCT imaging at P42 and P49 demonstrated in control rd10 animals a marked thinning of the outer nuclear layer (ONL) and the emergence of local retinal detachments (white arrow). Comparison of equivalent retinal areas in tamoxifen-treated rd10 animals revealed a greater preservation of ONL thickness (insets show magnified views of the ONL and retinal detachment). (B) Quantification of OCT-derived outer retinal thicknesses showed significantly greater preservation of the photoreceptor layer in tamoxifen-treated animals (grey lines) vs. control animals (black lines) (p values from 2-way ANOVA). (C) Electroretinographic (ERG) evaluation demonstrated significantly greater b-wave amplitudes in light- and dark-adapted responses at both P29 and P50 in tamoxifen-treated animals (grey lines) vs. control animals (black lines) (p values from 2-way ANOVA). (D) Visual acuity capabilities of P49 rd10 animals were evaluated under photopic conditions by automated assessment of optomotor responses. Sinusoidal gratings, rotating in a virtual cylinder at 12°/s, were presented at different spatial frequencies to each awake and unrestrained animal tested, and resulting optomotor responses were quantitated from the tracking of head movements as the ratio of the time during which head movement occurred in the same direction with stimulus movement to the time during which it occurred in the opposite direction ($T_{correct}/T_{incorrect}$). Data points (upper graph) indicate median ratios at each grating spatial frequency with the color areas indicating the upper and lower quartiles of the dataset. Comparison of responses indicated that tamoxifen-treated animals had greater optomotor responses to moving stimuli relative to control animals over a range of spatial frequencies presented. Estimations of visual threshold (lower graph), defined as the spatial frequency corresponding to 25% of the maximum optomotor response, significantly higher for tamoxifen-treated animals (p value from unpaired t-test with Welch correction), indicating that tamoxifen treatment resulted in a greater preservation of visual acuity function relative to controls.
Figure 4B:
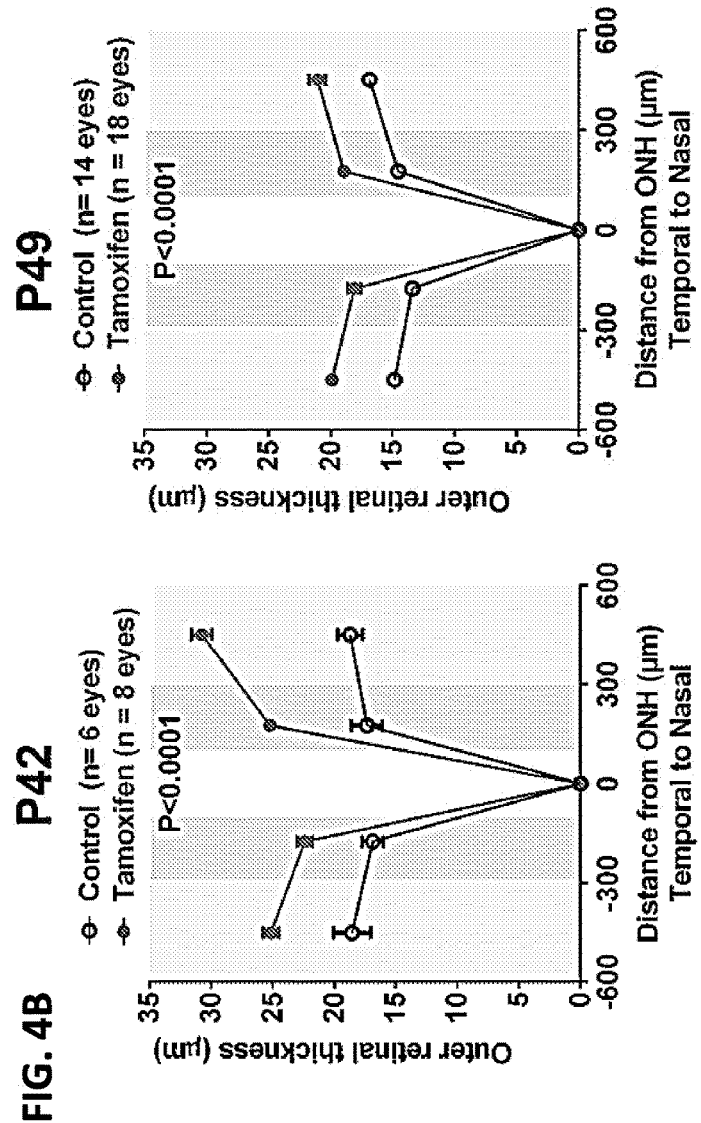
Figure 4C:
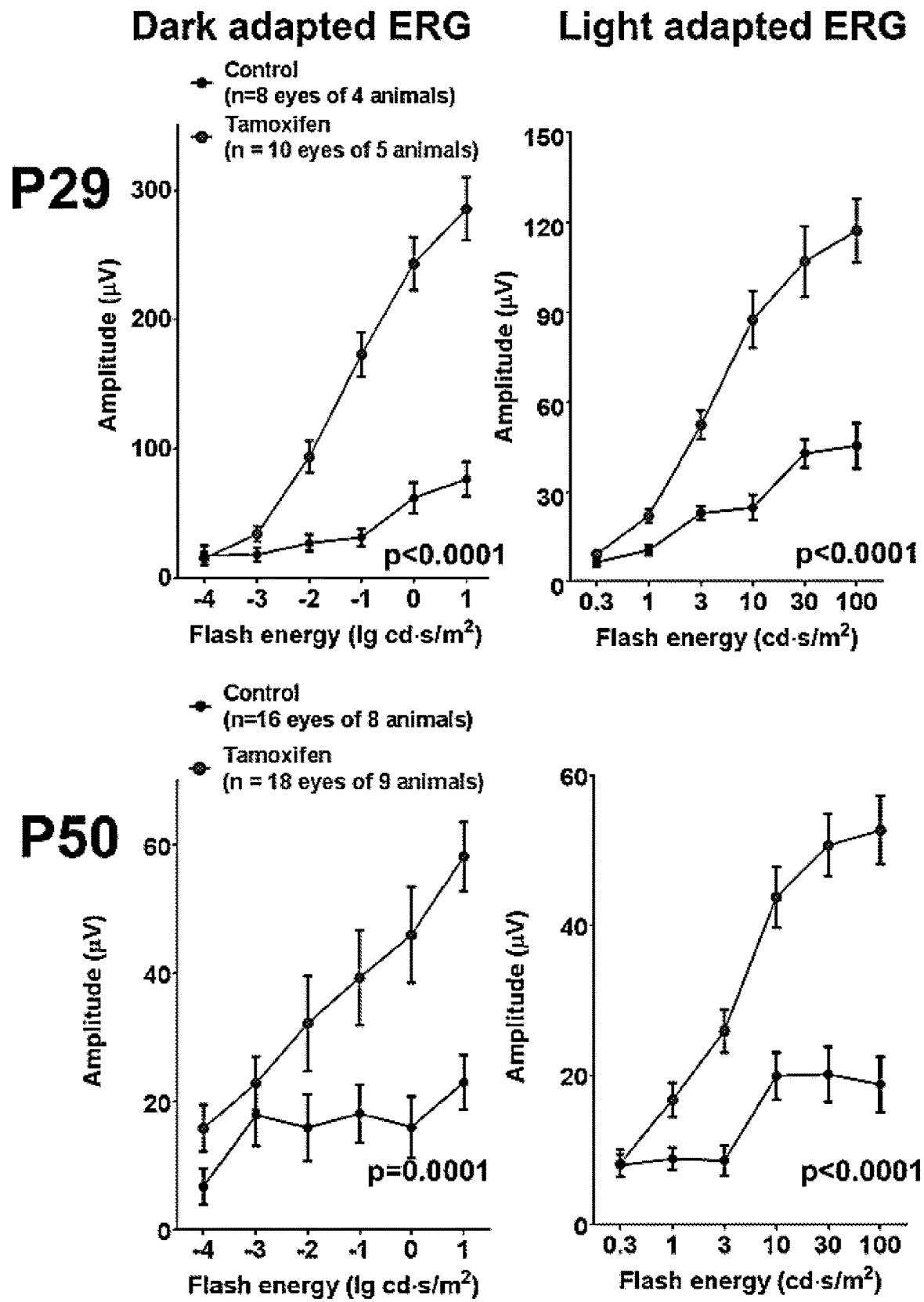

Tamoxifen Administration Provides Structural and Functional Rescue of Photoreceptor Degeneration in Rd10 Mouse Model for Retinitis Pigmentosa To evaluate whether tamoxifen treatment can provide photoreceptor protection in other etiologies of photoreceptor degeneration, such as retinitis pigmentosa (RP), the effect of tamoxifen-supplementation was investigated in rd10 mice, a mouse model of RP that is induced by a mutation in the photoreceptor-specific Pde6b gene (Chang et al., Vision Research 47:624-633, 2007), a causative gene in human RP (McLaughlin et al., Nature Genetics 4:130-134, 1993). In previous work, it was have found that activated microglia infiltrating the photoreceptor layer in the rd10 retina contribute non-cell autonomously to the rate of photoreceptor demise via phagocytic and proinflammatory mechanisms (Zhao et al., supra, 2015; Zabel et al., supra, 2016). It was hypothesized that the inhibition of microglial activation by tamoxifen could be helpful in delaying photoreceptor degeneration in RP. Thus, rd10 mice post-weaning at P21 were provided with the tamoxifen-supplemented chow and littermates that were fed standard chow were employed as controls. OCT measurements at P42 and P49 demonstrated that outer retina thicknesses in tamoxifen-treated animals were significantly greater than those in littermate controls (FIG. 4A, B). The prevalence of shallow retinal detachments at P49 were also lower in tamoxifen-treated vs. control animals (2/18 vs. 14/14, Chi-square statistic=24.9, p=0.00001). ERG evaluations at P29 and P50 demonstrated significantly larger b-wave amplitudes in dark- and light-adapted ERGs in tamoxifen-treated animals relative to littermate controls (FIG. 4C).

Figure 4D:
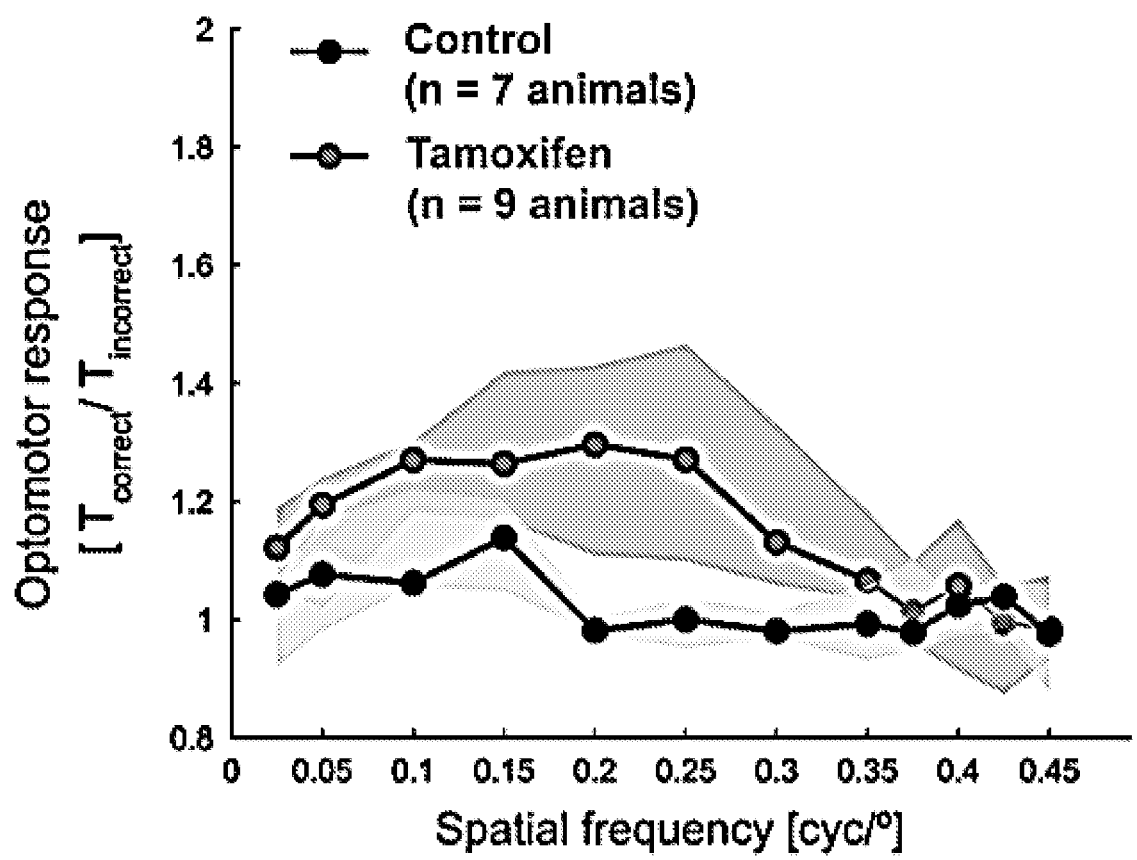
Figure 4D:
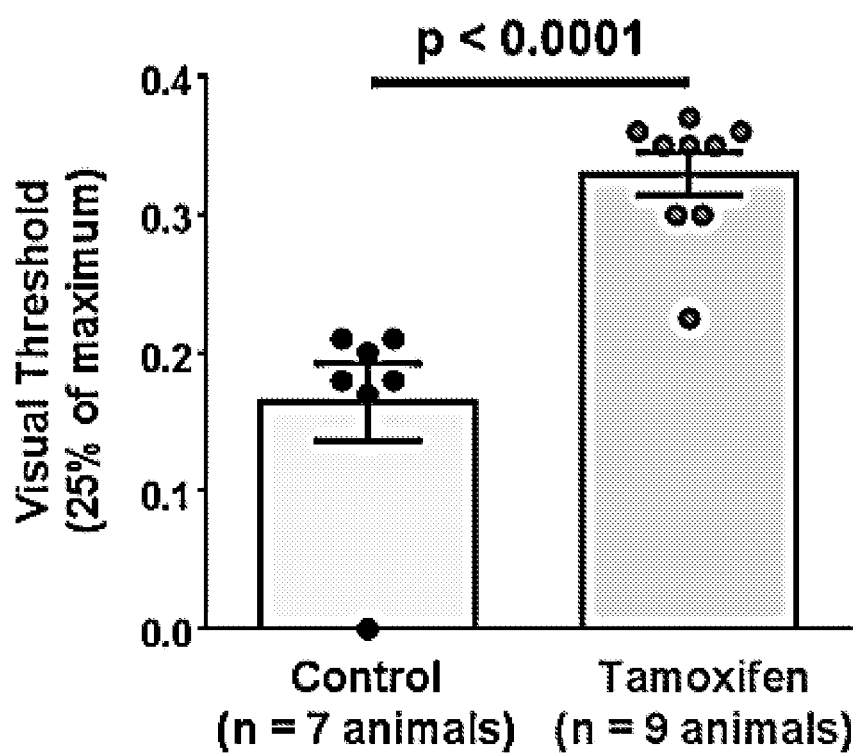

To assess if these rescue effects relate to an improved visual capability of treated animals, optomotor responses were assessed in experimental animals to presentations of visual stimuli. It was found that tamoxifen-treated animals at P49 demonstrated improved photopic optomotor responses over a broad range of spatial frequencies compared with littermate controls (FIG. 4D). Mean visual threshold, which approximates the maximum spatial frequency in the visual stimuli grating sufficient to elicit an optomotor response, was also significantly greater in tamoxifen-treated animals. Taken together, while tamoxifen treatment did not completely prevent progressive structural and functional deterioration in rd10 mice, there were statistically significant improvements in photoreceptor thickness and ERG responses relative to controls, which also translated to improved visual capability on a functional visual task. Thus, the tamoxifen was effective in treating these animals.

It is disclosed herein that tamoxifen, a selective estrogen receptor modulator (SERM), induces prominent structural and functional rescue of retinal photoreceptors in a well-established model of light-induced injury. It was observed that photoreceptor protection was correlated with suppression of microglial infiltration and activation, and an upregulation of pro-inflammatory cytokines. In vitro studies showed that tamoxifen directly inhibited pro-inflammatory cytokine production in cultured retinal microglia following LPS stimulation, and reduced the ability of BV2 microglia to induce 661W photoreceptor cell loss. It was further found that tamoxifen's protection against photoreceptor degeneration can be extended to other models of retinal disease, such as retinitis pigmentosa (RP); tamoxifen treatment was able to defer photoreceptor loss, photoreceptor function decrement, and visual function loss in a commonly-used mouse model of RP.

Tamoxifen, a drug approved for the treatment of metastatic breast cancer, exerts mixed agonist and antagonist actions at estrogen receptors (ER), depending on the target tissue and cell type (Riggs and Hartmann, The New England Journal of Medicine 348:618-629, 2003). Within the central nervous system (CNS), tamoxifen, as well as other SERMs, have been documented to exert complex effects on different cell types that together culminate in neuroprotective effects in various models of injury including spinal cord injury (Ismailoglu et al., Official Journal of the Neurosurgical Society of Australasia 17:1306-1310, 2010; de la Torre Valdovinos et al., Journal of Veterinary Medicine 2016: 9561968, 2016), penetrating brain injury (Arevalo et al., Journal of Neuroendocrinology 24:183-190, 2012; Franco Rodriguez et al., Brain Research Bulletin 98:64-75, 2013; Barreto et al., Frontiers in Aging nNeuroscience 6:132, 2014), and irradiation (Liu et al., Brain Research 1316:101-111, 2010).

Reported associations in the literature between tamoxifen and the retina have wholly centered on the occurrence of tamoxifen-related retinal toxicity that is evident as crystalline deposits, edema, or cystic cavitations appearing within the retina (Nayfield and Gorin, Journal of Clinical Oncology: Official Journal of the American Society of Clinical Oncology 14:1018-1026, 1996; Gualino et al., American journal of Ophthalmology 140:757-758, 2005; Bourla et al., American Journal of Ophthalmology 144:126-128, 2007). These features are found in a low percentage of patients receiving tamoxifen and are associated with variable visual symptoms and physiological changes (Gorin et al., American Journal of Ophthalmology 125:493-501, 1998; Salomao et al., Current Eye Research 32:345-352, 2007; Watanabe et al., Documenta Ophthalmologica Advances in Ophthalmology 120:137-143, 2010). However, as a result of these clinical observations, together with reports of tamoxifen inducing retinal cell damage in vitro (Cho et al., Invest Ophthalmol Vis Sci 53:5344-5353, 2012; Kim et al., Invest Ophthalmol Vis Sci 55:4747-4758, 2014), and the presently disclosed protective effects of tamoxifen, that can prevent or slow down photoreceptor degeneration, were not anticipated.

Contrary to the reports of retinal toxicity in human patients, no evidence was found in mouse models that the in vivo administration of tamoxifen resulted in ocular toxicity. In the experiments disclosed herein, tamoxifen-administered animals (80 mg/kg daily for 7 days) following LI demonstrated retinal structure and ERG function that was nearly identical to those in non-injured age-matched controls that had not been administered tamoxifen. When higher doses of tamoxifen were administered for longer periods (500 mg/kg oral dose every 5 days for 30 days), the emergence of retinal crystals or other retinal pathology was not detected, nor were marked changes in ERG amplitudes detected (Wang et al., The Journal of Neuroscience: The Official Journal of the Society for Neuroscience 36:2827-2842, 2016). Direct ocular administration of tamoxifen as an eye-drop (5 mg/ml eye drop delivered as a single 10 µl drop three times daily for 5 days) at doses high enough to induce Cre recombination via the Cre-ERT system (Hayashi and McMahon, Developmental Biology 244:305-318, 2002) also did not induce detectable retinal structural or functional changes (Boneva et al., Neuroscience 325:188-201, 2016). As a result, despite the low risk of retinal toxicity, tamoxifen has the potential to exert broadly evident clinical neuroprotection to endangered photoreceptors in retinal disease.

Without being bound by theory, the cellular mechanism underlying tamoxifen-mediated photoreceptor neuroprotection likely involves the modulation of retinal microglial activation. Studies have demonstrated that the specific modulation of microglial phagocytosis and activation results in structural and functional amelioration of photoreceptor degeneration in mouse models of RP (Peng et al., The Journal of Neuroscience: The Official Journal of the Society for Neuroscience 34:8139-8150, 2014; Zhao et al., supra, 2015; Zabel et al., supra, 2016). It is disclosed herein that tamoxifen directly suppressed proinflammatory cytokine production in activated retinal microglia and decreased microglial toxicity to 661W photoreceptor cells. Inhibition of IL1β signaling in mouse models of RP decreases photoreceptor apoptosis and rescues retinal function (Zhao et al., supra, 2015); tamoxifen in reducing microglial production of inflammatory cytokines including IL1β could contribute to photoreceptor rescue through this mechanism.

Without being bound by theory, as estrogen receptors (ERs) are additionally expressed by non-microglia CNS cell types, the neuroprotective effects of tamoxifen may also entail mechanisms involving neurons and macroglia cells via ER-dependent (Elzer et al., Journal of Cerebral Blood Flow and Metabolism: Official Journal of the International Society of Cerebral Blood Flow and Metabolism 30:935-942, 2010) and ER-independent (Zhang et al., Experimental Neurology 204:819-827, 2007) pathways. In the rodent and human retina, estrogen receptors have been found in multiple neuronal cell types and the retinal pigment epithelium (Ogueta et al., Invest Ophthalmol Vis Sci 40:1906-1911, 1999; Cascio et al., Exp Eye Res 85:166-172, 2007). As such, the effects of photoreceptor neuroprotection by tamoxifen could involve mechanisms within photoreceptors and their supporting RPE cells, such as via the modulation of the dynamics of the visual cycle which has demonstrated significant protection in a light injury model (Li et al., Human Molecular Genetics 24:4417-4428, 2015). In separate experiments, it was found that tamoxifen administration did not alter the dynamics of a-wave recovery of rod photoreceptors on ERG following a moderate visual pigment bleach, as such, tamoxifen is unlikely to exert neuroprotection through this particular mechanism.

Tamoxifen is also commonly used in the laboratory as a means to manipulate gene expression in transgenic mice that express tamoxifen-dependent Cre recombinases (CreER(T)) which are activated to enable DNA recombination upon tamoxifen-administration (Feil et al., Biochemical and Biophysical Research Communications 237:752-757, 1997). Transgenic mice developed include those with microglia-specific promoters that drive CreER(T) expression and genetic recombination in microglia upon tamoxifen administration in the brain (Goldmann et al., Nature Neuroscience 16:1618-1626, 2013; Parkhurst et al., Cell 155:1596-1609, 2013; Yona et al., Immunity 38:79-91, 2013) and the retina (Zhao et al., supra, 2015; Wang et al., The Journal of Neuroscience: The Official Journal of the Society for Neuroscience 36:2827-2842, 2016). It is disclosed herein that tamoxifen administration markedly suppresses of microglia activation and exerts neuroprotective effects in injury models indicate potential confounding effects in the interpretation of results obtained in CreER(T) systems and the need to institute experimental safeguards and controls.

Thus, it is disclosed herein that tamoxifen, a drug previously associated with retina toxicity, confers significant structural and functional protection to photoreceptors in both acute and genetic models of photoreceptor degeneration. The action of tamoxifen in suppressing retinal microglial activation and pro-inflammatory cytokine expression likely contributes to this protection, as supported by recent studies documenting the involvement of microglia in the acceleration of photoreceptor demise (Scholz et al., supra, 2015; Zhao et al., supra, 2015; Zabel et al., supra, 2016). Tamoxifen, and other SERMS with the same activities, constitute therapeutic agents for the treatment of photoreceptor degenerative diseases such as RP.

Example 7

Dose Effects on Tamoxifen-Mediated Rescue of Photoreceptor Degeneration in a Light Injury Model Young adult 10 to 15-week old wild type 129/SVE mice were subjected to light injury ($2\times10^4$ lux diffuse white light, 1 hour) following 24 hours of dark adaptation. Experimental animals were divided into three treatment groups: (1) standard diet (control) (n=26 eyes, in 13 animals, 6 female, 7 male), (2) diet supplemented with high-dose tamoxifen (≈80 mg/kg/day) (n=23 eyes, in 12 animals, 6 female, 6 male), and (3) diet supplemented with low-dose tamoxifen (≈10 mg/kg/day, approximately equivalent to a 0.81 mg/kg/day dose in an adult human) (n=30 eyes, in 15 animals, 8 female, 7 male). With regard to the dosage, the equivalent human dose was determined using Table 1 of "Guidance for Industry: Estimating the Maximum Safe Starting Dose in Initial Clinical Trials for Therapeutics in Adult Healthy Volunteers," U.S. Department of Health and Human Services, Food and Drug Administration, Center for Drug Evaluation and Research (CDER), July 2005, incorporated herein by reference, available on line at the FDA website (fda.gov), see fda.gov_downloads_Drugs/ . . . /Guidances/ UCM078932.pdf.

Figures 8A, 8B:
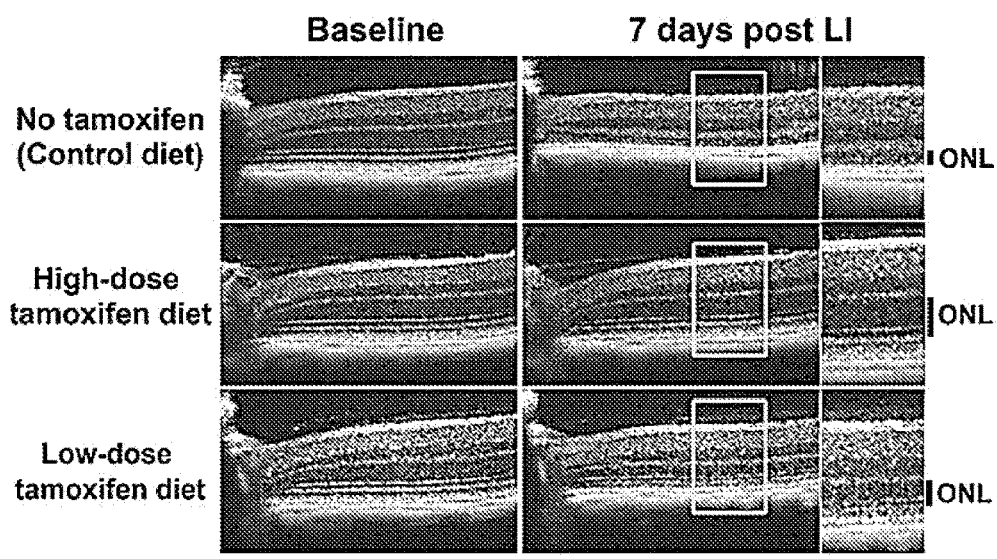
FIG. 8A-8B. Dose effects on tamoxifen-mediated rescue of photoreceptor degeneration in a light injury model. (A) Representative OCT images showing marked outer retinal disruption and atrophy in control animals with significant degeneration of the outer nuclear layer (ONL) (top row). Significant rescue of ONL degeneration was observed in animals provided either high—($\approx$80 mg/kg/day) middle row) or low-dose ($\approx$10 mg/kg/day, bottom) tamoxifen diets. (B) OCT quantification showing significant rescue of retinal thinning following light-injury in both high- and low-dose treated groups (comparisons of control group vs. high-dose group, control group vs. low-dose group, p<0.0001, 2-way ANOVA, Tukey's multiple comparisons test). There was slightly less rescue of retinal thickness in the low-dose group compared with the high-dose group (p=0.034-0.044), indicating a dose-dependent response in tamoxifen-mediated neuroprotection.
Figure 9:
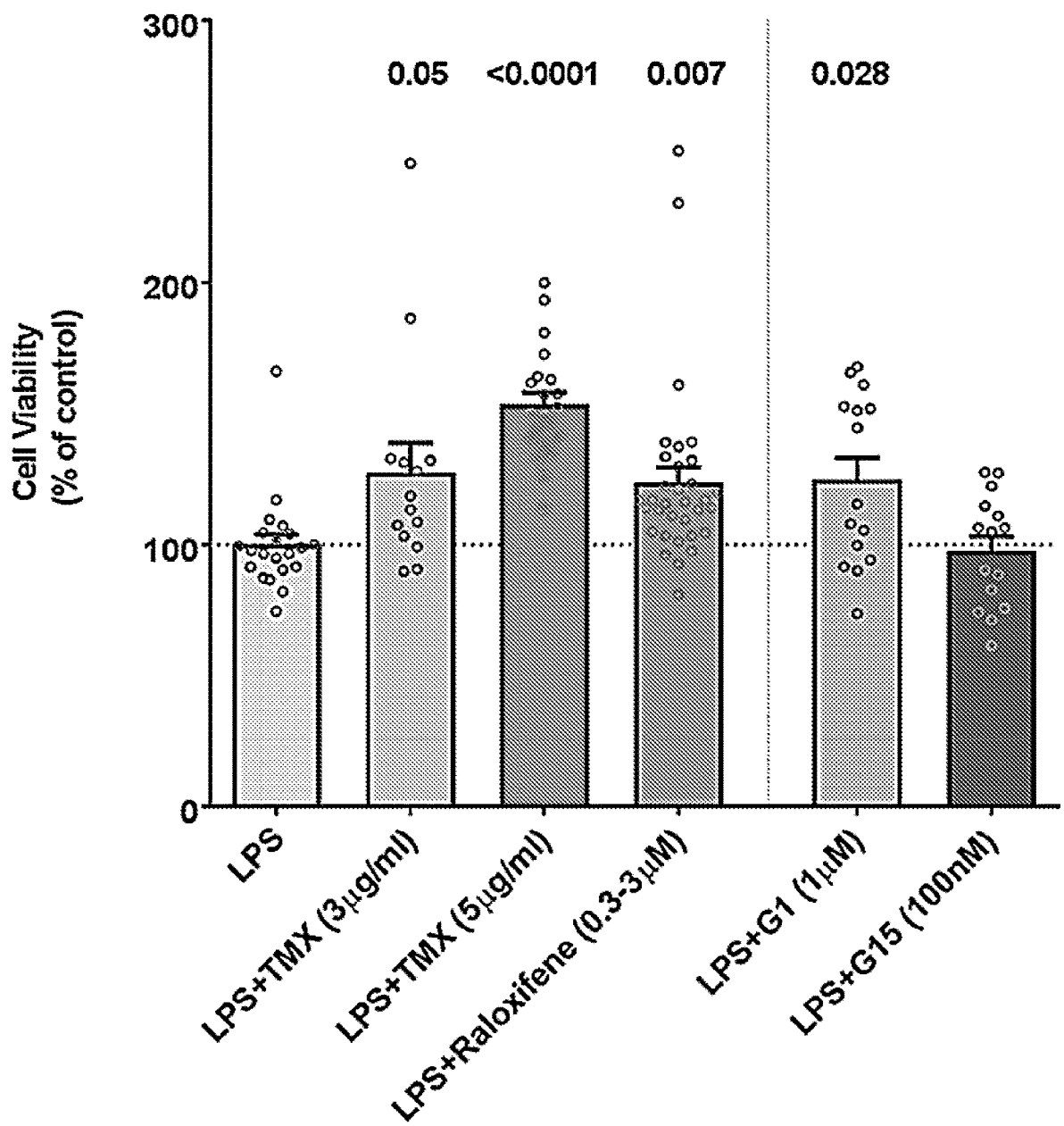
FIG. 9. Tamoxifen and Raloxifene, members of the class of SERM compounds, act on activated microglia to reduce their neurotoxicity to photoreceptors. Pre-treatment with tamoxifen, raloxifene, and GPR30 agonist, G-1, significantly reduced neurotoxicity of microglia-conditioned media, but GPR30 antagonist, G-15 did not (p values are for comparisons to the LPS only control, Kruskal-Wallis test with Dunn's multiple comparisons test, n=14-33 independent replicates for each group). Both tamoxifene and raloxifene provided suppression of neurotoxicity of microglia on phototoxicity.

Animals were administered tamoxifen 7 days prior to light injury (LI) and 7 days following LI. In vivo optical coherence tomographic (OCT) measurements of retinal thickness were obtained prior (baseline) and 7 days following LI; percentage decreases of retinal thickness at 7 days from baseline were computed in the central retina for distances 150 μm and 450 μm from the optic nerve in the horizontal and vertical meridians. FIG. 8A provides representative OCT images showing marked outer retinal disruption and atrophy in control animals with significant degeneration of the outer nuclear layer (ONL)(top row). Significant rescue of ONL degeneration was observed in animals provided either high—(middle row) or low-dose (bottom) tamoxifen diets. OCT quantification (FIG. 8B) showed significant rescue of retinal thinning following light-injury in both high- and low-dose treated groups (comparisons of control group vs. high-dose group, control group vs. low-dose group, p<0.0001, 2-way ANOVA, Tukey's multiple comparisons test). There was slightly less rescue of retinal thickness in the low-dose group compared with the high-dose group (p=0.034-0.044), indicating a dose-dependent response in tamoxifen-mediated neuroprotection.

Example 8

Tamoxifen and Raloxifene, Members of the Class of SERM Compounds, Act on Activated Microglia to Reduce their Neurotoxicity to Photoreceptors 661W photoreceptors cultured in 96-well plate ($4 \times 10^4$ cells/well) were exposed to conditioned media from LPS-stimulated (50 ng/ml) BV2 microglia (cultured in 6-well plate with a cell density of $4 \times 10^5$ cells/well) for 24 h. Prior to LPS-stimulation, BV2 microglia were pre-treated with tamoxifen (TMX, 3 and 5 μg/ml), raloxifene (dose range 0.3-3 μM), selective GPR30 agonist, G-1 (1 μM), and selective GPR30 receptor antagonist (100 nM). Cell viability of 661W photoreceptors were assessed using a MTT assay. Pre-treatment with tamoxifen, raloxifene, and GPR30 agonist, G-1, significantly reduced neurotoxicity of microglia-conditioned media, but GPR30 antagonist, G-15 did not (p values are for comparisons to the LPS only control, Kruskal-Wallis test with Dunn's multiple comparisons test, n=14-33 independent replicates for each group). The results indicate that both tested SERM compounds, tamoxifene and raloxifene, provided suppression of neurotoxicity of microglia on phototoxicity. This effect was phenocopied by agonism of the GPR30 receptor. Without being bound by theory, this outcome suggests that SERMs may be exerting these effects through this signaling pathway.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method of treating retinal degeneration in a subject, or protecting a subject from retinal degeneration, the method comprising administering to the subject a therapeutically effective amount of a selective estrogen receptor modulator (SERM) to treat the retinal degeneration in the subject, wherein the SERM is one or more of tamoxifen, afimoxifene, raloxifene, bazedoxifene, arzoxifene, desmethylarzoxifene, or a salt thereof, thereby treating the retinal degeneration in the subject, or protecting the subject from retinal degeneration.

2. The method of claim 1, wherein the SERM is a) tamoxifen or a salt thereof; or b) raloxifene or a salt thereof.

3. The method of claim 1, wherein the subject has retinitis pigmentosa, acute retinal degeneration, atrophic macular degeneration, or diabetic retinopathy.

4. The method of claim 1, wherein the SERM is administered orally.

5. The method of claim 3, wherein the SERM is tamoxifen, or a salt thereof, wherein the subject is human, and wherein the tamoxifen is administered at a dose of about 0.8 mg/kg to about 6.5 mg/kg daily.

6. The method of claim 3, wherein the SERM is tamoxifen, or a salt thereof, wherein the subject is human, and wherein the tamoxifen is administered orally at a dose of about 3.24 mg/kg to about 6.48 mg/kg daily.

7. The method of claim 3, wherein the SERM is tamoxifen, or a salt thereof, and wherein the tamoxifen is administered at a dose of 10 mg/kg to 80 mg/kg daily.

8. The method of claim 3, wherein the SERM is tamoxifen, or a salt thereof, and wherein the tamoxifen is administered orally at a dose of 40 mg/kg to 80 mg/kg daily.

9. The method of claim 1, wherein the SERM is administered for a minimum of three months.

10. The method of claim 1, wherein the subject is human.

11. The method of claim 1, wherein the SERM defers photoreceptor loss, reduces photoreceptor function decrement, reduces visual function loss, and/or suppresses retinal microglial activation and/or suppresses pro-inflammatory cytokine expression.

12. The method of claim 1, further comprising evaluating the vision of the subject.

13. The method of claim 12, comprising performing electroretinography on the subject.

14. The method of claim 1, wherein the subject does not have cancer.

15. The method of claim 1, wherein the subject does not have breast cancer.

16. The method of claim 1, wherein the SERM is tamoxifen.

17. The method of claim 1, further comprising selecting the subject with the retinal degeneration, prior to administering to the subject the therapeutically effective amount of the SERM.

18. The method of claim 1, wherein the method treats the retinal degeneration in the subject.

* * * * *